United States Patent [19]
Jacobs et al.

[11] Patent Number: 5,965,397
[45] Date of Patent: Oct. 12, 1999

[54] SECRETED PROTEINS AND POLYNUCLEOTIDES ENCODING THEM

[75] Inventors: Kenneth Jacobs, Newton; John M. McCoy, Reading; Edward R. LaVallie, Harvard; Lisa A. Racie; David Merberg, both of Acton; Maurice Treacy, Chestnut Hill; Vikki Spaulding, Billerica; Michael J. Agostino, Andover, all of Mass.

[73] Assignee: Genetics Institute, Inc., Cambridge, Mass.

[21] Appl. No.: 09/014,969

[22] Filed: Jan. 28, 1998

Related U.S. Application Data

[63] Continuation-in-part of application No. 08/792,511, Jan. 31, 1997
[60] Provisional application No. 60/080,233, Jan. 31, 1997.
[51] Int. Cl.$^6$ ..................................................... C12N 15/00
[52] U.S. Cl. .................... 435/69.1; 435/91.4; 435/252.3; 435/320.1; 536/23.1; 536/23.5; 536/24.31; 530/350
[58] Field of Search .................................. 435/69.1, 91.4, 435/252.3, 320.1; 536/23.1, 23.5, 24.31; 530/350

[56] References Cited

U.S. PATENT DOCUMENTS 5,536,637  7/1996  Jacobs .......................................... 435/6

FOREIGN PATENT DOCUMENTS

| 0510691 | 10/1992 | European Pat. Off. . |
|---|---|---|
| WO90/05780 | 5/1990 | WIPO . |
| WO90/14432 | 11/1990 | WIPO . |
| WO94/07916 | 4/1994 | WIPO . |
| WO96/17925 | 6/1996 | WIPO . |
| WO97/07198 | 2/1997 | WIPO . |
| WO97/25427 | 7/1997 | WIPO . |

OTHER PUBLICATIONS

Suzuki et al. (1986) An Introduction to Genetic Analysis, Third Ed., WH Freeman and Co., NY, NY,1986.
Ganong (1995) Review of Medical Physiology, 17th Ed., Appleton & Lange, Norwalk, Conn., 1995.
Hillier et al. (1995) EST Database, Accession No. T49148, 1995.
GenBank Accession No: N68677, Mar. 13, 1996.
GenBank Accession No: S58722, Jun. 18, 1993.
GenBank Accession No: U18466, Apr. 26, 1995.
GenBank Accession No: X92185, Oct. 20, 1995.
GenBank Accession No: Z68756, Mar. 13, 1996.
Adams MD et al. (1993) "3,400 new expressed sequence tags identify diversity of transcripts in human brain" Nature Genetics 4(3):256–267.
Jacobs K et al. (1995) "A novel method for isolating eukaryotic cDNA clones encoding secreted proteins" JCB Suppl 21A:19.
Kaufman RJ et al. (1989) "Effect of von Willebrand factor coexpression on the synthesis and secretion of factor VIII in CHO cells" Mol Cell Biol 9(3):1233–1242.
Kaufman RJ et al. (1989) "The phosphorylation state of eukaryotic initiation factor 2 alters translation efficiency of specific mRNAs" Mol Cell Biol 9(3):946–958.
Kaufman RJ et al. (1991) "Improved vectors for stable expression of foreign genes in mammalian cells by use of the untranslated leader sequence from EMC virus" Nucl Acids Res 19(16):4485–4490.
Hillier L et al. "The WashU–Merck EST Project", EMBL Accession No. N68677, za21g03.s1 *Homo sapiens* cDNA clone 293236 3', Mar. 14, 1996.

*Primary Examiner*—Robert A. Wax
*Assistant Examiner*—Enrique D. Longton
*Attorney, Agent, or Firm*—Lahive & Cockfield, LLP; Suzanne A. Sprunger; Scott A. Brown

[57] ABSTRACT

Novel polynucleotides and the proteins encoded thereby are disclosed.

14 Claims, 2 Drawing Sheets

5,965,397

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 2509 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
TATGAAATAA AAATAAAAGG TAGACAATAC ACAGATTTAT TGTATGAGTG TTGAAGAAAT        60

ACTCAGAAAG CAAGTGTTGT TTAAAATCAA GTTGTGATGG TATAAACGAC ATTTCCTAGC       120

AGGCAGCCTG ATGGTCACTG GTCGTGCCTA GTACCGTAGG ATAAATGAGA CATTGCCTCT       180

TACTTGCTTT AGAGAAGTGG GCACTCCCCT CCCCTCACCC AAGAGAGACT TATTTGGGCA       240

TTATTGAAAA AAATTTGTCA TTGTCTGTGA GCCTGTTATA GGTAATTTTA ATAATTACAT       300

GTTAACATTA CAACTTTGAG TATAAGAGGT TTTGGCATCT TTGAACACAT TATAGGCTTT       360

AGTGAGAACC AGAGAAACAT ATTTGGTCTT TCACAGAAAT TAACCCTAAC CCTCCGAGTT       420

CCTTAGTATT CACCCCTGTG CAATCTATGT TTATTGTAGC AAATTGAGAA AATGCATAAA       480

TGGTTAAAGA AATAAAAGCT TCCATCAGTC AACCAAACAA AAGCATTGAT GATTTAGATT       540

ATGTCTTTGC AGTTGTTTTC TTTTATCTAT GTTCTCAATT AAGAACCTTT GCATTGTAAG       600

CAACAGTAAG TGACTCTGGT TAATGTCAGC AGAGAAGTGG GCTTGTTGTG AGGTCCCTGG       660

GCAGCTCACC ATGGTCAAAG AGTGTGGACA TGAATTACTG TGACCTAGGC AGTCACCCCA       720

TTTGTCTTTT TTCTGCTTTT TTTTAATAAA ACCAGAATAT ATTATACATG GTGCGTGTTC       780

CTCACTTTCT GTGCCTTGGG AAACACTGCT GTGATGGGCA TAACGAGTCT CAAAGAGGAA       840

GGATCTACGG GTAAAGGAGA TGCATGCAGA AACAGCCTCT AATTTGTCAG TAAGCCATGC       900
```

```
AGTTAGCAGG TGTATTAGTC TGTTCTCATG CTGATAATAA AGATATACCA GAGACTGGGT      960

AATTTATAAA GGAAAGAGGT TTAATGGACT CACAGGTTGG GAAGGCCTCA CACTCATGGC     1020

AGAAGGTGAA GGAGGAGCAA AGGCACATCT TACATGGCGG CAGACAAGAG AAAGTGTACG     1080

GGGGAGTTGC CCTTTATAAA ACCATCAGAT CTCGTGAGAC TTATTCACTA CCACGAGAAC     1140

AGTAAGGGGG GAACTGCCCC CCCCATAATT CAGTTATCTC CACCTAGCCC TGTCCTTGAT     1200

ACATGGGGAT TATTACAGTT CAAGGTGAGA TTTGGGTGGG GACACAGCCA ATCATATCA      1260

GCAGGGAATG GTTTAGCAGT TCACAATGAC AAGCCTGGGT GCAAGGATAA CCCCAAGATA     1320

CTGCTTCGGC CAAGCTGATA TTTGGACGGA GGACACAGAA AATAAATTCT TAAGCTCTGG     1380

AGCTAGGGAG AACAGAGGAT GTAAAAAAAA AATACTCTGG ACAAGCTTAG TGGCAGTCAA     1440

GGAAAGCAGA AGCAGTCAAG CAGTTTTACA GGGCAGTGCA CGCTTTCCAT GTAGATGCTA     1500

TGTTGTCATT CATTTCTATT TTCTATTTCT TATTTTATTT TATTTTATTT TATTTGAGAC     1560

AGAGGCTCGC TCTACTGCCC AAGCTGGAGT GCAGTGGCAT AATCTTGGCT CACTGCAACC     1620

TCCGCCTTCT GGGACCAAGT GATTCTCCTG CCTCAGCTTC CCAAGTAGCT GGCATTACTG     1680

GTGCCTGCCG CCATGCCCGG CTAATTTTTT GTATTTTTAG TAGAGACAGG GTTCCACCAT     1740

GTTGGCCAGG CTGGTCTCAA ACTCCTGACT TAAGGTGATC TGTCTGCCTT GGCCTCCGAA     1800

AGTGTTGGTG AGCCACCACA CCCGGCCTCA TTTCTGTTTT GGAGTTCAGA TTTACAAAGG     1860

GACTAGAGTA CTTTTTTTCC TCATAGAGAA TAAAATATCC TCTTTAAAAT TTGCCCTTTT     1920

GCTTTATTTT TATTTAATTT TTTTGAGATG GAGTTTTGCT CTTGTGGCCC AGGCTTGAGT     1980

GCAATGGCAC AATCTTGGCT TACTGCAACC TCTGCCTCCC AGGTTCAAGT GATTTTCCTG     2040

CCTCAGCCTC CCAAGTAGCT GGGATTACAG GTACTCGTCA CCACGCCCAG CTAATTTCTT     2100

TGTATTTTTA GTAAAGATGG GGTTTCGCCA TGTTAGCCAG GCTGGTCTTG AACTTCTGAC     2160

CTCAGGCGAT CTGCCCACTT TGGGAGGCCA CGGCGGGTGG ATCACCTGAA GTCAGGAGTT     2220

TGAGACTAGT CTGACCAACA TGGTGAAACC CTGTCTCTAC TAAAAATACA AGAATTAGC      2280

TGGGCATGGT GGCGGGCGCC TGTAATCCCA GCTACTGGGG AGGCTGAGTC AGGAGAATTG     2340

CTTGAACCCA GGAGGCGGAG GCTGCCGTGA GCCAAGATCG TGCCATTGCA CTTCAGCCTG     2400

GGCAACAAGA GTGAAAATCA GTCTCAAAAA ATAAAAAGAA AAAGGAAAAA TGGCTAAAAT     2460

GGTAAACCCC ATGTTACCTG TTTTTTTAAA TCACAAAAAA AAAAAAAA               2509

(2) INFORMATION FOR SEQ ID NO:2:

(i) SEQUENCE CHARACTERISTICS:
        (A) LENGTH: 44 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

Met Glu Ala Phe Ile Ser Leu Thr Ile Tyr Ala Phe Ser Gln Phe Ala
 1               5                  10                  15

Thr Ile Asn Ile Asp Cys Thr Gly Val Asn Thr Lys Glu Leu Gly Gly
                20                  25                  30

Leu Gly Leu Ile Ser Val Lys Asp Gln Ile Cys Phe
            35                  40

(2) INFORMATION FOR SEQ ID NO:3:
```

```
    (i) SEQUENCE CHARACTERISTICS:
         (A) LENGTH: 384 base pairs
         (B) TYPE: nucleic acid
         (C) STRANDEDNESS: double
         (D) TOPOLOGY: linear (ii) MOLECULE TYPE: cDNA (xi) SEQUENCE DESCRIPTION: SEQ ID NO:3:

AAGAAAGAAA AGCTCAGAGG CAAGCAGCAA AAAATCAAAT GTATGACGAT TACTACTATT      60

ATGGTCCACC TCATATGCCC CCTCCAACAA GAGGTCGAGG GCGTGGAGGT AGAGGTGTTT     120

ATGGATATCC TCCAGATTAT TATGGATATG AAGATTATTA TGATTATTAT GGTTATGATT     180

ACCATAACTA TCGTGGTGGA TATGAAGATC CATACTATGG TTATGAAGAT TTTCAAGTTG     240

GAGCTAGAGG AAGGGGTGGT AGAGGAGCAA GGGGTGCTGC TCCATCCAGA GGTCGTGGGG     300

CTGCTCCTCC CCGCGGTAGA GCCGGTTATT CACAGAGAGG AGGTCCTGGA TCAGCAAGAG     360

GCGTTCGAGG TGCGAGAGGA GGTG                                           384

(2) INFORMATION FOR SEQ ID NO:4:

(i) SEQUENCE CHARACTERISTICS:
         (A) LENGTH: 114 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:4:

Met Thr Ile Thr Thr Ile Met Val His Leu Ile Cys Pro Leu Gln Gln
1               5                  10                  15

Glu Val Glu Gly Val Glu Val Glu Val Phe Met Asp Ile Leu Gln Ile
            20                  25                  30

Ile Met Asp Met Lys Ile Met Ile Ile Met Val Met Ile Thr Ile
        35                  40                  45

Thr Ile Val Val Asp Met Lys Ile His Thr Met Val Met Lys Ile Phe
50                  55                  60

Lys Leu Glu Leu Glu Glu Gly Val Val Glu Glu Gln Gly Val Leu Leu
65                  70                  75                  80

His Pro Glu Val Val Gly Leu Leu Leu Pro Ala Val Glu Pro Val Ile
                85                  90                  95

His Arg Glu Glu Val Leu Asp Gln Gln Glu Ala Phe Glu Val Arg Glu
            100                 105                 110

Glu Val (2) INFORMATION FOR SEQ ID NO:5:

(i) SEQUENCE CHARACTERISTICS:
         (A) LENGTH: 413 base pairs
         (B) TYPE: nucleic acid
         (C) STRANDEDNESS: double
         (D) TOPOLOGY: linear (ii) MOLECULE TYPE: cDNA (xi) SEQUENCE DESCRIPTION: SEQ ID NO:5:

ACAATCATTT GTGCTATGTT TTTAATTTTC TAAAGCACCT TGATGACAGT GAGTGTCCAG      60

TGGNGAAGCA TCCTCTATTG AACAACCCTC AAAAATTTTT TTGCCAAGTC CTAAGTTGAT     120

AGCTTAAAGT AAAAAGTGAA AATTATAGTT TCATTAGGAC TTGGTGTAAA GAAATCCCCT     180

CCCCCCTTCC CCAAAGGGAT ACTGCAGTTA TATCACATAC CAATAGGCA CCACGATGAA      240
```

```
GATCAGAGCT TATACTTAAT TAAGGTTTTA TACACACCAG TTCCCCAGTA AATGCAAATT      300

TAACAAGAAA ATCAGACATG TCATATGTTC AAAATGCTCA TGGCAAACAA TCATTTTGCA      360

TTCCTGCAAA TAAAATTGTT TTATACTGTA AAAAAAAAAA AAAAAAAAA AAA              413
```

(2) INFORMATION FOR SEQ ID NO:6:

(i) SEQUENCE CHARACTERISTICS:
        (A) LENGTH: 1045 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

```
AGTAGTTCTA TGAGGATTGC AAGTCATAGG TGTGTGTGGC ATATCAGTCC ATCTCCCTCA       60

TCTCCATTCT CAGTTTCTTC CCCACAAAAT TTGGAATCAA AGCTTTTATG ACGTTTGCCA      120

ATTGCAGAAC TTCTTCAGCT AAGGTTAATT TGACGCTATG ATAAAACTGA GAGATGTCAA      180

AAAGCCTCTT AGAAATTTTA ATCTTGAAAG ACTTTTCAGG GTATCTCATT TTTTAGGTGG      240

GGGTGGCAGG TGTATTTCTT TTTTAACAAA TAAAAGGCAT TTAAGTAAAA CTAAAATGAA      300

AAAAGTAGGC CTTCTGACAT TGTGTACTTG GTGGTTCTGT CCCTCTGCCT GTAACAAATC      360

TCATTTTTGT TACCAAGAAC TGTATGAAAG AAGTAAATCC ACCCCGATTC TGTATGATTA      420

ATTCCATCTG TGTTTGTCAT TTCTGACTGG AAAACTTCTT ACTCCATACC TTGTTCGATA      480

TGGAGGACAA ATAATTGGAT TGTCTGATAA GTCTGCCAAT AAACTATCCA GAAATAGCAA      540

GTGTAATAGT CCCCACTATA CGAATTTTAT GGTTTGTATA AACACTAACA TTTTCCCCTT      600

CTGTAGTTGT ATGAAAAAAC AAATATTGTT AGCATAGTAG ATAAATTGTT ATGAAATACC      660

AGAAAAAAAA ATCTGTATCT TTTACTGAGA ACACCCAATA CCCAGATAAA TGACTGTATC      720

AGGATTTCAT TTGCATGTTA GTCCACAGAG TTGCCCAGAA CCCTAAATTT ATTCATAAGA      780

GAAAATATTG ATTAATTATT GGTCATTCCT CATAAGTGTA GCTGTTGATG TGTGCGTCTG      840

ATTATTGCTT TTTTAATTTT ATGAAAATTG TGTAAAATTA CATTTTTTTT CCAGGGGAGA      900

AAAAAACATC AAACAAAAAC ATCTAAATCA TCCTTTTTGT TCTTTTTCAG TTTTTAACCA      960

CTTTTAGGTT TTCCCCTTAC AGAAACCACA GAAATATTCC CTTAGAATAA AATAGTATAT     1020

TTGTATTTGA AAAAAAAAAA AAAAA                                           1045
```

(2) INFORMATION FOR SEQ ID NO:7:

(i) SEQUENCE CHARACTERISTICS:
        (A) LENGTH: 87 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Met Ile Lys Leu Arg Asp Val Lys Lys Pro Leu Arg Asn Phe Asn Leu
 1               5                  10                  15

Glu Arg Leu Phe Arg Val Ser His Phe Leu Gly Gly Gly Arg Cys
             20                  25                  30

Ile Ser Phe Leu Thr Asn Lys Arg His Leu Ser Lys Thr Lys Met Lys
                 35                  40                  45

Lys Val Gly Leu Leu Thr Leu Cys Thr Trp Trp Phe Cys Pro Ser Ala
 50                  55                  60
```

Cys Asn Lys Ser His Phe Cys Tyr Gln Glu Leu Tyr Glu Arg Ser Lys
65                  70                  75                  80

Ser Thr Pro Ile Leu Tyr Asp
                85

(2) INFORMATION FOR SEQ ID NO:8:

(i) SEQUENCE CHARACTERISTICS:
        (A) LENGTH: 2999 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

```
CCTAAAATCA TCAAAGTCAC GGTGAAGACT CCCAAAGAGA AAGAGGAGTT CGCGGTGCCC      60
GARAACAGCT CGGTTCAGCA GTTTAAGGAA GCGATTTCGA AACGCTTCAA ATCCCAAACC     120
GATCAGCTAG TGCTGATTTT TGCCGGAAAA ATCTTAAAAG ATCAAGATAC CTTGATCCAG     180
CATGGCATCC ATGATGGGCT GACTGTTCAC CTTGTCATCA AAAGCARAA CCGACCTCAG      240
GGCCAGTCCA CGCAGCCTAG CAATGCCGCG GGAACTAACA CTACCTCGGC GTCGACTCCC     300
AGGAGTAACT CCACACCTAT TTCCACAAAT ASCAACCCGT TTGGGTTGGG GAGCCTGGGA     360
GGACTTGCAG GCCTTARCAG CCTGGGCTTG AGCTCGACCA ACTTCTCTGA GCTCCAGAGC     420
CAGATGCAGC AGCAGCTTAT GGCCAGCCCT GAGATGATGA TCCAAATAAT GGAAAATCCC     480
TTTGTTCAGA GCATGCTTTC GAATCCCGAT CTGATGAGGC AGCTCATTAT GGCTAATCCA     540
CAGATGCAGC AATTGATTCA GAGAAACCCA GAAATCAGTC ACCTGCTCAA CAACCCAGAC     600
ATAATGAGGC AGACACTCGA AATTGCCAGG AATCCAGCCA TGATGCAAGA GATGATGAGA     660
AATCAAGACC TGGCTCTTAG CAATCTAGAA AGCATCCCAG GTGGCTATAA TGCTTTACGG     720
CGCATGTACA CTGACATTCA AGAGCCGATG CTGAATGCCG CACAAGAGCA GTTTGGGGGT     780
AATCCATTTG CCTCCGTGGG GAGTAGTTCC TCCTCTGGGG AAGGTACGCA GCCTTCCCGC     840
ACAGAAAATC GCGATCCACT ACCCAATCCA TGGGCACCAC CGCCAGCTAC CCAGAGTTCT     900
GCAACTACCA GCACGACCAC AAGCACTGGT AGTGGGTCTG GCAATAGTTC CAGCAATGCT     960
ACTGGGAACA CCGTTGCTGC CGCTAATTAT GTCGCCAGCA TCTTTAGTAC CCCAGGCATG    1020
CAGAGCCTGC TGCAACAGAT AACTGAAAAC CCCCAGCTGA TTCAGAATAT GCTGTCGGCG    1080
CCCTACATGA GAAGCATGAT GCAGTCGCTG AGCCAGAATC CAGATTTGGC TGCACAGATG    1140
ATGCTGAATA GCCCGCTGTT TACTGCAAAT CCTCAGCTGC AGGAGCAGAT GCGGCCACAG    1200
CTCCCAGCCT TCCTGCAGCA GATGCAGAAT CCAGACACAC TATCAGCCAT GTCAAACCCA    1260
AGAGCAATGC AGGCTTTAAT GCAGATCCAG CAGGGGCTAC AGACATTAGC CACTGAAGCA    1320
CCTGGCCTGA TTCCGAGCTT CACTCCAGGT GTGGGGGTGG GGGTGCTGGG AACCGCTATA    1380
GGCCCTGTAG GCCAGTCACC CCCATAGGC CCCATAGGCC CTATAGTCCC TTTTACCCCC     1440
ATAGGCCCCA TTGGGCCCAT AGGACCCACT GGCCCTGCAG CCCCCCCTGG CTCCACCGGC    1500
TCTGGTGGCC CCACGGGGCC TACTGTGTCC AGCGYTGCAC YTAGTGAAAC CACGAGTCCT    1560
ACATCAGAAT YTGGACCCAA CCAGCAGTTC ATTCAGCAAA TGGTGCAGGC CCTGGCTGGA    1620
GCAAATGCTC CACAGCTGCC GAATCCAGAA GTCAGATTTC AGCAACAAST GGAACAGCTC    1680
AACGCAATGG GGTTCTTAAA CCGTGAAGCA AACTTGCAGG CCCTAATAGC AACAGGAGGC    1740
GACATCAATG CAGCCATTGA AAGGCTGCTG GGCTCCCAGC CATCGTAATC ACATTTCTGT    1800
```

-continued

```
ACCTGGAAAA AAAATGTATC TTATTTTTGA TAATGGCTCT TAAATCTTTA AACACACACA    1860

CAAAATCGTT CTTTACTTTC ATTTTGATTC TTTTAAATCT GTCTAGTTGT AAGTCTAATA    1920

TGATGCATTT TAAGATGGAG TCCCTCCCTC CTACTTCCCT CACTCCCTTT CTCCTTTGCT    1980

TATTTTTCCT ACCTTCCCTT CCTCTTGTCT CCCCACTCCC TCCCTCTTTG TTTCCTTCCT    2040

TCCTTATTTC CTTAGTTTC CTTCCTTAGC CGTTTTGAGT GGTGGGAATC AATGCTGTTT     2100

CACTCAAAAG TGTTGCATGC AAACACTTCT CTTTATTCTG CATTTATTGT GATTTTTGGA    2160

AACAGGTATC AACCTTCACA GTTGGGTGAA CAAGTGTTGT CCTACAGATG TCCAATTTAT    2220

TTGCATTTTT AAACATTAGC CTATGATAGT AATTTAATGT AGAATGAAGA TATTAAAAAC    2280

AGAAGCAAAT TATTTGAAGC TCTCTAATTT GTGGTACGAT ATTGCTTATT GTGACTTTGG    2340

CATGTATTTT TGCTAGCAAA ATGCTGTAAG ATTTATACCA TTGATCTTTT TTGCTATATT    2400

TGTATACAGT ACAGTAAGCA CAATTGGCAC TGTACATCTA AAAATATTAC AGTAGAATCT    2460

GAGTGTAATA TGTGTAACCA AAATGAGAAA GAATACAAGA AATGTTTCTG GAGCTAGTTA    2520

TGTCTCACAA TTTTGTAGAA TCTTACAGCA TCTTTGATAA ACTTCTCAGT GAAAATGTTG    2580

GCTAGGCAAG TTCAGTTAAA ATATAGTAGA AATGTTTATC CTGGTATCTC TAAGTATACA    2640

TTTAATTGTA CAGAAAATTT ACAGTGTAAC ATTGTGTCAA CATTTGCAGA TTGACTGTAT    2700

ATGACCTTAA TCTTTGTGCA GCCTGAAGGA TCAGTGTAGT AATGCCAGGA AAGTGCTTTT    2760

TACCTAAGAC TTCCTTCTCA GCTTCTCCCA TAAAGAGACC CTAATATGCA TTTTGATTTG    2820

TAATTGGAAA TGTAACTTTC ACTGAAAGTG TCATGTGATG TTTGCATTAC TTTTAACTGC    2880

TATGTATAAA GGAAAGTGTG TCTTTTGACT TCATCAGTTA TTTCTCTTGT GCACAGAGAA    2940

AAATGCATTA AAAATGACTA AAAAAAATAA AAAATTAAAA AATGAAAAAA AAAAAAAA     2999
```

(2) INFORMATION FOR SEQ ID NO:9:

(i) SEQUENCE CHARACTERISTICS:
        (A) LENGTH: 454 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

```
Met Gln Gln Gln Leu Met Ala Ser Pro Glu Met Met Ile Gln Ile Met
1               5                   10                  15

Glu Asn Pro Phe Val Gln Ser Met Leu Ser Asn Pro Asp Leu Met Arg
            20                  25                  30

Gln Leu Ile Met Ala Asn Pro Gln Met Gln Gln Leu Ile Gln Arg Asn
        35                  40                  45

Pro Glu Ile Ser His Leu Leu Asn Asn Pro Asp Ile Met Arg Gln Thr
    50                  55                  60

Leu Glu Ile Ala Arg Asn Pro Ala Met Met Gln Glu Met Met Arg Asn
65                  70                  75                  80

Gln Asp Leu Ala Leu Ser Asn Leu Glu Ser Ile Pro Gly Gly Tyr Asn
                85                  90                  95

Ala Leu Arg Arg Met Tyr Thr Asp Ile Gln Glu Pro Met Leu Asn Ala
            100                 105                 110

Ala Gln Glu Gln Phe Gly Gly Asn Pro Phe Ala Ser Val Gly Ser Ser
        115                 120                 125

Ser Ser Ser Gly Glu Gly Thr Gln Pro Ser Arg Thr Glu Asn Arg Asp
    130                 135                 140
```

```
Pro Leu Pro Asn Pro Trp Ala Pro Pro Ala Thr Gln Ser Ser Ala
145                 150                 155                 160

Thr Thr Ser Thr Thr Thr Ser Thr Gly Ser Gly Ser Gly Asn Ser Ser
        165                 170                 175

Ser Asn Ala Thr Gly Asn Thr Val Ala Ala Asn Tyr Val Ala Ser
            180                 185                 190

Ile Phe Ser Thr Pro Gly Met Gln Ser Leu Leu Gln Gln Ile Thr Glu
        195                 200                 205

Asn Pro Gln Leu Ile Gln Asn Met Leu Ser Ala Pro Tyr Met Arg Ser
    210                 215                 220

Met Met Gln Ser Leu Ser Gln Asn Pro Asp Leu Ala Ala Gln Met Met
225                 230                 235                 240

Leu Asn Ser Pro Leu Phe Thr Ala Asn Pro Gln Leu Gln Glu Gln Met
                245                 250                 255

Arg Pro Gln Leu Pro Ala Phe Leu Gln Gln Met Gln Asn Pro Asp Thr
            260                 265                 270

Leu Ser Ala Met Ser Asn Pro Arg Ala Met Gln Ala Leu Met Gln Ile
        275                 280                 285

Gln Gln Gly Leu Gln Thr Leu Ala Thr Glu Ala Pro Gly Leu Ile Pro
    290                 295                 300

Ser Phe Thr Pro Gly Val Gly Val Gly Val Leu Gly Thr Ala Ile Gly
305                 310                 315                 320

Pro Val Gly Pro Val Thr Pro Ile Gly Pro Ile Gly Pro Ile Val Pro
                325                 330                 335

Phe Thr Pro Ile Gly Pro Ile Gly Pro Ile Gly Pro Thr Gly Pro Ala
            340                 345                 350

Ala Pro Pro Gly Ser Thr Gly Ser Gly Gly Pro Thr Gly Pro Thr Val
        355                 360                 365

Ser Ser Xaa Ala Xaa Ser Glu Thr Thr Ser Pro Thr Ser Glu Xaa Gly
    370                 375                 380

Pro Asn Gln Gln Phe Ile Gln Gln Met Val Gln Ala Leu Ala Gly Ala
385                 390                 395                 400

Asn Ala Pro Gln Leu Pro Asn Pro Glu Val Arg Phe Gln Gln Gln Xaa
                405                 410                 415

Glu Gln Leu Asn Ala Met Gly Phe Leu Asn Arg Glu Ala Asn Leu Gln
            420                 425                 430

Ala Leu Ile Ala Thr Gly Gly Asp Ile Asn Ala Ala Ile Glu Arg Leu
        435                 440                 445

Leu Gly Ser Gln Pro Ser
    450

(2) INFORMATION FOR SEQ ID NO:10:

(i) SEQUENCE CHARACTERISTICS:
        (A) LENGTH: 2925 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

SACTGAACCA CGGAGCTCAC CCTGGACAGT ATCACTCCGT GGAGGAAGAC TGTGAGACTG      60

TGGCTGGAAG CCAGATTGTA GCCACACATC CGCCCCTGCC CTACCCCAGA GCCCTGGAGC     120

AGCAACTGGC TGCAGATCAC AGACACAGTG AGGATATGAG TGTAGGGGTG AGCACCTCAG     180

CCCCTCTTTC CCCAACCTCG GGCACAAGCG TGGGCATGTC TACCTTCTCC ATCATGGACT     240
```

```
ATGTGGTGTT CGTCCTGCTG CTGGTTCTCT CTCTTGCCAT GGGCTCTAC  CATGCTTGTC    300
GTGGCTGGGG CCGGCATACT GTTGGTGAGC TGCTGATGGC GGACCGCAAA ATGGGCTGCC    360
TTCCGGTGGC ACTGTCCCTG CTGGCCACCT TCCAGTCAGC CGTGGCCATC CTGCGTGTGC    420
CGTCAGAGAT CTACCGATTT GGGACCCAAT ATTGGTTCCT GCGCTGCTGC TACTTTCTGG    480
GGCTGCTGAT ACCTGCACAC ATCTTCATCC CCGTTTTCTA CCGCCTGCAT CTCACCAGTG    540
CCTATGAGTA CCTGGAGCTT CGATTCAATA AAACTGTGCG AGTGTGTGGA ACTGTGACCT    600
TCATCTTTCA GATGGTGATC TACATGGGAG TTGTGCTCTA TGCTCCGTCA TTGGCTCTCA    660
ATGCAGTGAC TGGCTTTGAT CTGTGGCTGT CCGTGCTGGC CCTGCGCATT GTCTGTACCG    720
TCTATACAGC TCTGGGTGGG CTGAAGGCCG TCATCTGGAC AGATGTGTTC CAGACACTGG    780
TCATGTTCCT CGGGCAGCTG GCAGTTATCA TCGTGGGGTC AGCCAAGGTG GGCGGCTTGG    840
GGCGTGTGTG GGCCGTGGCT TCCCAGCACG GCCGCATCTC TGGGTTTGAG CTGGATCCAG    900
ACCCCTTTGT GCGGCACACC TTCTGGACCT TGGCCTTCGG GGGTGTCTTC ATGATGCTCT    960
CCTTATACGG GGTGAACCAG GCTCAGGTGC AGCGGTACCT CAGTTCCCGC ACGGAGAAGG   1020
CTGCTGTGCT CTCCTGTTAT GCAGTGTTCC CCTTCCAGCA GGTGTCCCTC TGCGTGGGCT   1080
GCCTCATTGG CCTGGTCATG TTCGCGTATT ACCAGGAGTA TCCCATGAGC ATTCAGCAGG   1140
CTCAGGCAGC CCCAGACCAG TTCGTCCTGT ACTTTGTGAT GGATCTCCTG AAGGGCCTGC   1200
CAGGCCTGCC AGGGCTCTTC ATTGCCTGCC TCTTCAGCGG CTCTCTCAGC ACTATATCCT   1260
CTGCTTTTAA TTCATTGGCA ACTGTTACGA TGGAAGACCT GATTCGACCT TGGTTCCCTG   1320
AGTTCTCTGA AGCCCGGGCC ATCATGCTTT CCAGAGGCCT TGCCTTTGGC TATGGGCTGC   1380
TTTGTCTAGG AATGGCCTAT ATTTCCTCCC AGATGGGACC TGTGCTGCAG GCAGCAATCA   1440
GCATCTTTGG CATGGTTGGG GGACCGCTGC TGGGACTCTT CTGCCTTGGA ATGTTCTTTC   1500
CATGTGCTAA CCCTCCTGGT GCTGTTGTGG GCCTGTTGGC TGGGCTCGTC ATGGCCTTCT   1560
GGATTGGCAT CGGGAGCATC GTGACCAGCA TGGGCTTCAG CATGCCACCC TCTCCCTCTA   1620
ATGGGTCCAG CTTCTCCCTG CCCACCAATC TAACCGTTGC CACTGTGACC ACACTGATGC   1680
CCTTGACTAC CTTCTCCAAG CCCACAGGGC TGCAGCGGTT CTATTCCTTG TCTTACTTAT   1740
GGTACAGTGC TCACAACTCC ACCACAGTGA TTGTGGTGGG CCTGATTGTC AGTCTACTCA   1800
CTGGGAGAAT GCGAGGCCGG TCCCTGAACC CTGCAACCAT TTACCCAGTG TTGCCAAAGC   1860
TCCTGTCCCT CCTTCCGTTG TCCTGTCAGA AGCGGCTCCA CTGCAGGAGC TACGGCCAGG   1920
ACCACCTCGA CACTGGCCTG TTTCCTGAGA AGCCGAGGAA TGGTGTGCTG GGGACAGCA    1980
GAGACAAGGA GGCCATGGCC CTGGATGGCA CAGCCTATCA GGGGAGCAGC TCCACCTGCA   2040
TCCTCCAGGA GACCTCCCTG TGATGTTGAC TCAGGACCCC GCCTCTGTCC TCACTGTGCC   2100
AGGCCATAGC CAGAGGCCAC CCTGTAGTAC AGGGATGAGT CTTGGTGTGT CTGCAGGGA    2160
CAGGCCTGGA TGATCTAGCT CATACCAAAG GACCTTGTTC TGAGAGGTTC TTGCCTGCAG   2220
GAGAAGCTGT CACATCTCAA GCATGTGAGG CACCGTTTTT CTCGTCGCTT GCCAATCTGT   2280
TTTTTAAAGG ATCAGGCTCG TAGGGAGCAG GATCATGCCA GAAATAGGGA TGGAAGTGCA   2340
TCCTCTGGGA AAAGATAAT  GGCTTCTGAT TCAACATAGC CATAGTCCTT TGAAGTAAGT   2400
GGCTAGAAAC AGCACTCTGG TTATAATTGC CCCAGGGCCT GATTCAGGAC TGACTCTCCA   2460
CCATAAAACT GGAAGCTGCT TCCCCTGTAG TCCCCATTTC AGTACCAGTT CTGCCAGCCA   2520
CAGTGAGCCC CTATTATTAC TTTCAGATTG TCTGTGACAC TCAAGCCCCT CTCATTTTTA   2580
TCTGTCTACC TCCATTCTGA AGAGGGAGGT TTTGGTGTCC CTGGTCCTCT GGGAATAGAA   2640
```

```
GATCCATTTG TCTTTGTGTA GAGCAAGCAC GTTTTCCACC TCACTGTCTC CATCCTCCAC    2700

CTCTGAGATG ACACTTAAG AGACGGGCA AATGTGGATC CAAGAAACCA GGGCCATGAC     2760

CAGGTCCACT GTGGAGCAGC CATCTATCTA CCTGACTCCT GAGCCAGGCT GCCGTGGTGT    2820

CATTTCTGTC ATCCGTGCTC TGTTTCCTTT TGGAGTTTCT TCTCCACATT ATCTTTGTTC    2880

CTGGGGAATA AAACTACCA TTGGACCTAG AAAAAAAAAA AAAAA                      2925
```

(2) INFORMATION FOR SEQ ID NO:11:

(i) SEQUENCE CHARACTERISTICS:
  (A) LENGTH: 635 amino acids
  (B) TYPE: amino acid
  (C) STRANDEDNESS:
  (D) TOPOLOGY: linear (ii) MOLECULE TYPE: protein (xi) SEQUENCE DESCRIPTION: SEQ ID NO:11:

```
Met Ser Val Gly Val Ser Thr Ser Ala Pro Leu Ser Pro Thr Ser Gly
1               5                   10                  15

Thr Ser Val Gly Met Ser Thr Phe Ser Ile Met Asp Tyr Val Val Phe
            20                  25                  30

Val Leu Leu Leu Val Leu Ser Leu Ala Ile Gly Leu Tyr His Ala Cys
        35                  40                  45

Arg Gly Trp Gly Arg His Thr Val Gly Glu Leu Leu Met Ala Asp Arg
    50                  55                  60

Lys Met Gly Cys Leu Pro Val Ala Leu Ser Leu Leu Ala Thr Phe Gln
65                  70                  75                  80

Ser Ala Val Ala Ile Leu Arg Val Pro Ser Glu Ile Tyr Arg Phe Gly
                85                  90                  95

Thr Gln Tyr Trp Phe Leu Arg Cys Cys Tyr Phe Leu Gly Leu Leu Ile
            100                 105                 110

Pro Ala His Ile Phe Ile Pro Val Phe Tyr Arg Leu His Leu Thr Ser
        115                 120                 125

Ala Tyr Glu Tyr Leu Glu Leu Arg Phe Asn Lys Thr Val Arg Val Cys
    130                 135                 140

Gly Thr Val Thr Phe Ile Phe Gln Met Val Ile Tyr Met Gly Val Val
145                 150                 155                 160

Leu Tyr Ala Pro Ser Leu Ala Leu Asn Ala Val Thr Gly Phe Asp Leu
                165                 170                 175

Trp Leu Ser Val Leu Ala Leu Arg Ile Val Cys Thr Val Tyr Thr Ala
            180                 185                 190

Leu Gly Gly Leu Lys Ala Val Ile Trp Thr Asp Val Phe Gln Thr Leu
        195                 200                 205

Val Met Phe Leu Gly Gln Leu Ala Val Ile Ile Val Gly Ser Ala Lys
    210                 215                 220

Val Gly Gly Leu Gly Arg Val Trp Ala Val Ala Ser Gln His Gly Arg
225                 230                 235                 240

Ile Ser Gly Phe Glu Leu Asp Pro Asp Pro Phe Val Arg His Thr Phe
                245                 250                 255

Trp Thr Leu Ala Phe Gly Gly Val Phe Met Met Leu Ser Leu Tyr Gly
            260                 265                 270

Val Asn Gln Ala Gln Val Gln Arg Tyr Leu Ser Ser Arg Thr Glu Lys
        275                 280                 285

Ala Ala Val Leu Ser Cys Tyr Ala Val Phe Pro Phe Gln Gln Val Ser
    290                 295                 300
```

```
Leu Cys Val Gly Cys Leu Ile Gly Leu Val Met Phe Ala Tyr Tyr Gln
305                 310                 315                 320

Glu Tyr Pro Met Ser Ile Gln Gln Ala Gln Ala Ala Pro Asp Gln Phe
            325                 330                 335

Val Leu Tyr Phe Val Met Asp Leu Leu Lys Gly Leu Pro Gly Leu Pro
            340                 345                 350

Gly Leu Phe Ile Ala Cys Leu Phe Ser Gly Ser Leu Ser Thr Ile Ser
            355                 360                 365

Ser Ala Phe Asn Ser Leu Ala Thr Val Thr Met Glu Asp Leu Ile Arg
370                 375                 380

Pro Trp Phe Pro Glu Phe Ser Glu Ala Arg Ala Ile Met Leu Ser Arg
385                 390                 395                 400

Gly Leu Ala Phe Gly Tyr Gly Leu Leu Cys Leu Gly Met Ala Tyr Ile
                405                 410                 415

Ser Ser Gln Met Gly Pro Val Leu Gln Ala Ala Ile Ser Ile Phe Gly
                420                 425                 430

Met Val Gly Gly Pro Leu Leu Gly Leu Phe Cys Leu Gly Met Phe Phe
            435                 440                 445

Pro Cys Ala Asn Pro Pro Gly Ala Val Val Gly Leu Leu Ala Gly Leu
450                 455                 460

Val Met Ala Phe Trp Ile Gly Ile Gly Ser Ile Val Thr Ser Met Gly
465                 470                 475                 480

Phe Ser Met Pro Pro Ser Pro Ser Asn Gly Ser Ser Phe Ser Leu Pro
                485                 490                 495

Thr Asn Leu Thr Val Ala Thr Val Thr Thr Leu Met Pro Leu Thr Thr
                500                 505                 510

Phe Ser Lys Pro Thr Gly Leu Gln Arg Phe Tyr Ser Leu Ser Tyr Leu
            515                 520                 525

Trp Tyr Ser Ala His Asn Ser Thr Thr Val Ile Val Val Gly Leu Ile
            530                 535                 540

Val Ser Leu Leu Thr Gly Arg Met Arg Gly Arg Ser Leu Asn Pro Ala
545                 550                 555                 560

Thr Ile Tyr Pro Val Leu Pro Lys Leu Leu Ser Leu Leu Pro Leu Ser
                565                 570                 575

Cys Gln Lys Arg Leu His Cys Arg Ser Tyr Gly Gln Asp His Leu Asp
                580                 585                 590

Thr Gly Leu Phe Pro Glu Lys Pro Arg Asn Gly Val Leu Gly Asp Ser
            595                 600                 605

Arg Asp Lys Glu Ala Met Ala Leu Asp Gly Thr Ala Tyr Gln Gly Ser
610                 615                 620

Ser Ser Thr Cys Ile Leu Gln Glu Thr Ser Leu
625                 630                 635

(2) INFORMATION FOR SEQ ID NO:12:

(i) SEQUENCE CHARACTERISTICS:
        (A) LENGTH: 3111 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

CCGCCATGTC CCCTCCCATC CCAGGTCCCG TTGTAACACA GGACATTACC ACGTATCACA      60

CGGTGTTTCT TTTGGCCATT TTAGGAGGAA TGGCTTTCAT ACTTTTGGTT TTGCTGTGTC     120
```

-continued

| | |
|---|---|
| TCCTTTTATA TTATTGCAGG AGGAAGTGCT TGAAACCTCG TCAGCACCAC AGAAAACTGC | 180 |
| AGCTCCCTGC AGGACTGGAG AGTTCCAAAA GAGACCAGTC CACGTCCATG TCACACATTA | 240 |
| ACTTGCTGTT TTCACGCCGA GCGTCAGAAT TCCCTGGCCC GCTGTCCGTC ACCAGCCACG | 300 |
| GCCGCCCCGA GGCCCCCGGC ACGAAGGAAC TGATGAGTGG AGTCCATTTG GAAATGATGT | 360 |
| CTCCGGGCGG CGAAGGGGAC CTGCACACCC CCATGCTCAA GCTCTCCTAC AGCACCTCCC | 420 |
| AGGAATTTAG CTCCCGGGAG GAGCTCCTCT CTTGCAAGGA AGAGGATAAA GCCAGATCT | 480 |
| CCTTTGATAA CCTCACTCCA AGTGGGACGC TGGGGAAAGA CTACCATAAG TCAGTGGAGG | 540 |
| TTTTTCCCTT AAAGGCAAGA AAATCTATGG AAAGAGAAGG CTACGAGTCC TCGGGCAATG | 600 |
| ATGACTACAG GGGTAGTTAC AACACCGTGC TCTCACAGCC TTTATTTGAA AAGCAGGACA | 660 |
| GAGAAGGTCC AGCCTCCACG GGAAGCAAAC TCACCATTCA GGAACATCTG TACCCCGCGC | 720 |
| CTTCATCACC TGAGAAAGAA CAGCTGCTGG ACCGCAGACC CACTGAATGT ATGATGTCGC | 780 |
| GATCAGTAGA TCACCTCGAG AGACCTACGT CCTTCCCACG GCCCGGCCAG TTAATCTGCT | 840 |
| GCAGTTCTGT CGACCAGGTC AATGACAGCG TTTACAGGAA AGTACTGCCT GCCTTGGTCA | 900 |
| TCCCGGCTCA TTATATGAAA CTCCCCGGGG ACCACTCCTA TGTCAGCCAG CCCCTCGTCG | 960 |
| TCCCGGCTGA TCAGCAGCTT GAGATAGAAA GACTACAGGC TGAGCTGTCC AATCCCCATG | 1020 |
| CCGGGATCTT CCCACACCCG TCCTCACAGA TCCAGCCCCA GCCCTGTCT TCCCAGGCCA | 1080 |
| TCTCTCAGCA GCACCTGCAG GATGCGGGCA CCCGGGAGTG GAGCCCTCAG AACGCATCCA | 1140 |
| TGTCGGAGTC TCTCTCCATC CCAGCTTCCC TGAACGACGC GGCTTTGGCT CAGATGAACA | 1200 |
| GTGAGGTGCA GCTCCTGACT GAAAAGCCCT GATGGAGCTT GGGGGTGGGA AGCCGCTTCC | 1260 |
| GCACCCCCGG GCGTGGTTCG TCTCCTTGGA TGGCAGGTCC AACGCTCACG TTAGACATTC | 1320 |
| ATACATTGAT CTCCAAAGAG CTGGAAGGAA CGGAAGTAAT GATGCCAGTT TGGACTCTGG | 1380 |
| CGTAGATATG AATGAACCAA AATCAGCCCG GAAGGGAAGG GGAGATGCTT TGTCTCTGCA | 1440 |
| GCAGAACTAC CCGCCCGTCC AAGAGCACCA GCAGAAAGAG CCTCGAGCCC CAGACAGCAC | 1500 |
| GGCCTACACG CAGCTCGTGT ACCTGGATGA CGTGGAACAG AGTGGTAGCG AATGTGGGAC | 1560 |
| CACGGTCTGT ACCCCCGAGG ACAGTGCCCT GCGATGCTTG TTGGAGGGGT CGAGTCGGAG | 1620 |
| AAGTGGTGGC CAGCTGCCCA GCCTGCAGGA GGAGACGACC AGACGGACTG CGGATGCCCC | 1680 |
| CTCGGAGCCA GCAGCCAGCC CCCACCAGAG AAGATCTGCC CACGAGGAAG AGGAAGACGA | 1740 |
| TGATGATGAT GACCAAGGAG AAGACAAGAA AAGCCCCTGG CAGAAACGGG AGGAGAGGCC | 1800 |
| CCTGATGGCG TTTAACATTA AATGAGCTAT CGCAGACCCA CCTGACTGTG GAATATAAAA | 1860 |
| TTGCCAAATA TCCTTTCTCA TGGAAGCGCG TACCCGTTCG TGGAGGAAAC GGAACGGCAG | 1920 |
| CCCAGCCGTG GGACGGACGT GGACGTTTAC TGCATTCCTG TTTGCCGTGT AAATGTTAGA | 1980 |
| AAGGAATTAA AGTTATTACT CGGAATAAAG GATGACTTTG GCGGATGTCG CCCCTGCAAG | 2040 |
| GAGGTGGCTG AAAGTGGTGT CCAGATGTCC TTCCGAGGAC TCGGCGTATC CGCCACCAGG | 2100 |
| GACATTAAGA AACCGCACGT GATGTCGCTA TGCTCTAACG ATCACCTCAG TTCTCCCTCG | 2160 |
| GATTCTGGGA ACAGATGAAA CTTTTTGCAT CGCTTGAGTC ATTTTTATCA CAATAATCCT | 2220 |
| ACTGTGAAGC TGTCGTTGAG AACTTAGGTT GGCACGTAGC GTCTCAAGGT ATGCGTTCTC | 2280 |
| TCAAAGGAAA GCTATGCATC GCTGCTTCGT TGTCTGATTT TGCTTAGATT TTGCTTTGGT | 2340 |
| TAGGTTGCGT TTTGGGGTTT GCCTTTTTTT GTTGTCGCTT AAATGCAATT TGGTTGTAAA | 2400 |
| GATTTGATTC CTTTGTGTTC ATCTGTTCCG CTTCTCAGCG GTCCATCTCA GCGTCTCCCT | 2460 |
| TCAGGAACCG CTGAGTGTCC TCTCTTAACA TCCAAGCCTT TTAATGAAAT CGTACTGAAA | 2520 |

```
TCTGTATCAG CTAAGAGTCC TCCAATCCTG GTCCCATTAA CTCCAAGTGC CTTTTTGACA    2580

GTGACAACAG ACAGTCCCTC GCTTTTTGTT GTTGTTGGTT TTCTTAACCC CTTTAATGGA    2640

ACTGCCTGGA TTTTATACAG TTATTAAAGG ATGTCTCTTT TGCTTTAAAC TGCATGCTGC    2700

CAAGTGCCAT TTGGGGTCAG CATCCTCGTT TCAACACAGT GTGCTCTCTA GTTATCATGT    2760

GTAACGTGGG TTCTGTTTAG CGAAGATAGA CTAGAGGACA CGTTAGAGAT GCCCTTCCCT    2820

GCTCCATCCC TGTGGCACCA TTATGGTTTT TTGGCTGTTT GTATATACGG TTACGTATTA    2880

ACTCTGGAAT CCTATGGGCT CATCTTGCTC ACCCAATGTG GGAGTCTGGT TTGAGCAAGC    2940

GAGCTGAATG TGACTATTAA AAAAAATTTA AAAAAAAAAA AGAAAATCTT ATGTACTATC    3000

CAAAAGTGCC AGAAKGACTC TTCTGTGCAT TCTTCTTAAA GAGCTGSTKG GTTATCCAAA    3060

AATGAAAATT CAAATAAAC TCTGAAGAAA AGGAANAAAA AAAAAAAAA A              3111

(2) INFORMATION FOR SEQ ID NO:13:

(i) SEQUENCE CHARACTERISTICS:
        (A) LENGTH: 408 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

Met Ser Pro Pro Ile Pro Gly Pro Val Val Thr Gln Asp Ile Thr Thr
1               5                  10                  15

Tyr His Thr Val Phe Leu Leu Ala Ile Leu Gly Gly Met Ala Phe Ile
            20                  25                  30

Leu Leu Val Leu Leu Cys Leu Leu Tyr Tyr Cys Arg Arg Lys Cys
        35                  40                  45

Leu Lys Pro Arg Gln His His Arg Lys Leu Gln Leu Pro Ala Gly Leu
    50                  55                  60

Glu Ser Ser Lys Arg Asp Gln Ser Thr Ser Met Ser His Ile Asn Leu
65                  70                  75                  80

Leu Phe Ser Arg Arg Ala Ser Glu Phe Pro Gly Pro Leu Ser Val Thr
                85                  90                  95

Ser His Gly Arg Pro Glu Ala Pro Gly Thr Lys Glu Leu Met Ser Gly
            100                 105                 110

Val His Leu Glu Met Met Ser Pro Gly Gly Glu Gly Asp Leu His Thr
        115                 120                 125

Pro Met Leu Lys Leu Ser Tyr Ser Thr Ser Gln Glu Phe Ser Ser Arg
    130                 135                 140

Glu Glu Leu Leu Ser Cys Lys Glu Glu Asp Lys Ser Gln Ile Ser Phe
145                 150                 155                 160

Asp Asn Leu Thr Pro Ser Gly Thr Leu Gly Lys Asp Tyr His Lys Ser
                165                 170                 175

Val Glu Val Phe Pro Leu Lys Ala Arg Lys Ser Met Glu Arg Glu Gly
            180                 185                 190

Tyr Glu Ser Ser Gly Asn Asp Asp Tyr Arg Gly Ser Tyr Asn Thr Val
        195                 200                 205

Leu Ser Gln Pro Leu Phe Glu Lys Gln Asp Arg Glu Gly Pro Ala Ser
    210                 215                 220

Thr Gly Ser Lys Leu Thr Ile Gln Glu His Leu Tyr Pro Ala Pro Ser
225                 230                 235                 240

Ser Pro Glu Lys Glu Gln Leu Leu Asp Arg Arg Pro Thr Glu Cys Met
```

```
            245                 250                 255
Met Ser Arg Ser Val Asp His Leu Glu Arg Pro Thr Ser Phe Pro Arg
            260                 265                 270

Pro Gly Gln Leu Ile Cys Cys Ser Ser Val Asp Gln Val Asn Asp Ser
        275                 280                 285

Val Tyr Arg Lys Val Leu Pro Ala Leu Val Ile Pro Ala His Tyr Met
    290                 295                 300

Lys Leu Pro Gly Asp His Ser Tyr Val Ser Gln Pro Leu Val Val Pro
305                 310                 315                 320

Ala Asp Gln Gln Leu Glu Ile Glu Arg Leu Gln Ala Glu Leu Ser Asn
                325                 330                 335

Pro His Ala Gly Ile Phe Pro His Pro Ser Ser Gln Ile Gln Pro Gln
            340                 345                 350

Pro Leu Ser Ser Gln Ala Ile Ser Gln Gln His Leu Gln Asp Ala Gly
        355                 360                 365

Thr Arg Glu Trp Ser Pro Gln Asn Ala Ser Met Ser Glu Ser Leu Ser
    370                 375                 380

Ile Pro Ala Ser Leu Asn Asp Ala Ala Leu Ala Gln Met Asn Ser Glu
385                 390                 395                 400

Val Gln Leu Leu Thr Glu Lys Pro
                405
```

(2) INFORMATION FOR SEQ ID NO:14:

(i) SEQUENCE CHARACTERISTICS:
        (A) LENGTH: 2447 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

```
GGCACCTTCC CTGCGAAAAG GCGGGCGGAG CCGAAAACCA AACAAACGAC TTCTGAGAGA    60
TTGGGGGCGG GACTGACGGC GGCCGGCTTA GCTTCCAGAG CCAAGGCCTT CCGCCGAGTT   120
GGTTTTTGGG TTGTTGATCG CGGTGGCCGG GCGGTCTGCG GTCGGGCTGA GACACGCGGA   180
GCAATGGCGA CCTTTGTGAG CGAGCTGGAG GCGGCCAAGA AGAACTTAAG CGAGGCCCTG   240
GGGGACAACG TGAAACAATA CTGGGCTAAC CTAAAGCTGT GGTTCAAGCA GAAGATCAGC   300
AAAGAGGAGT TTGACCTTGA AGCTCATAGA CTTCTCACAC AGGATAATGT CCATTCTCAC   360
AATGATTTCC TCCTGGCCAT TCTCACGCGT TGTCAGATTT TGCTTTCTAC ACCAGATGGT   420
GCTGGATCTT TGCCTTGGCC AGGGGGTTCC GCAGCAAAAC CTGGAAAACC CAAGGGAAAG   480
AAAAAGCTTT CTTCTGTTCG TCAGAAATTT GATCATAGAT CCAGCCTCA  AAATCCTCTC   540
TCAGGAGCCC AGCAATTTGT GGCAAAGGAT CCCCAAGATG ATGACGACTT GAAACTTTGT   600
TCCCACACAA TGATGCTTCC CACTCGAGGC CAGCTTGAAG GGAGAATGAT AGTGACTGCT   660
TATGAGCATG GGCTGGACAA TGTCACCGAG GAGGCTGTTT CAGCTGTTGT CTATGCTGTG   720
GAGAATCACC TTAAAGATAT ACTGACGTCA GTTGTGTCAA GAAGGAAAGC TTATCGGTTA   780
CGAGATGGTC ATTTTAAATA TGCCTTTGGC AGTAACGTGA CCCCGCAGCC ATACCTGAAG   840
AATAGTGTAG TAGCTTACAA CAACTTAATA GAAAGCCCTC CAGCTTTTAC TGCTCCCTGT   900
GCTGGTCAGA ATCCAGCTTC TCACCCACCC CCTGATGATG CTGAGCAGCA GGCTGCACTC   960
CTGCTGGCAT GCTCCGGAGA CACTCTACCT GCATCTTTGC CTCCGGTGAA CATGTACGAT  1020
CTTTTTGAAG CTTTGCAGGT GCACAGGGAA GTCATCCCTA CACATACTGT CTATGCTCTT  1080
```

```
AACATTGAAA GGATCATCAC GAAACTCTGG CATCCAAATC ATGAAGAGCT GCAGCAAGAC    1140

AAAGTTCACC GCCAGCGCTT GGCAGCCAAG GAGGGGCTTT TGCTGTGCTA AATTAGGATT    1200

TGAGGGTGTG GGACCCTCAC CAAATTCATT GATTACTGAA AATTGAATGT TTTTTGGGTC    1260

CACATTTCAA GGCTGAAGTG TATAGTGTAT ATATAACCTT TCCTATGGAA ATGTGACATT    1320

GAGTACATTT TGTGTTGCTA TTGTGAAGCC ATTAATATAA ATCTTTGGTA ATGACCCATA    1380

TCTCTATATG TATGTGTTCC CAGTTGTGGG AGCAGGCACT AATGAAATCC TGTGCCTGGA    1440

ATGGAGATAT TTAGGTACCT GAGGCTTAGT GTCCTGTGGT CTGCATGTAA GATAGATGAC    1500

ATCCTAGAAC AAAGAAGCTG TTTTAACTTA ATCCCCCTGA TCAGCAGGAT ATCTGTGTGT    1560

TCAGTGACAT CATACATTCT GTATCTAGAA GTCTAAAATT TCTGCCTTTC TCCTAAAGAA    1620

TGTGTTCTTG CATTTTGGTT GAAATAACCT ACACAGTGTT AAAAATCAGA TACCTCCTTT    1680

AGTGACCAGT TCAAATTTTA ATAGCGATAG GTAGCCCCTG AGAAATTTAT CACTATAACT    1740

CCACAGGAAA TATGACTTGG AAGTGCTCTG TGTACTAAAC AAAATAAAGC CCCTCTTTGC    1800

ATTTAAAACC AAAGTCAAAA CAAAACTCTT GTAATGCAAT TAATTAACTT TATGTCTTCC    1860

CATGACTCAA GTTTTGTTAA ATATGCCCAA AAACTTTGAT TGGCAGTTTC TTCGGTTAAT    1920

TATTCCTATA GAATGTATTT TAAGAAATCT ATACAAATTG GATATATGCT TGGTAATTCT    1980

CCAGTTTCTA GGAGGTACCT ATTTCTACCG TTTCAAGTGA TGAAGTGAAA ATAATTTACA    2040

TTCGATAGTG TTACTGATAA CAAACCTACT TAAGAGATAT GTTGCTTTTT ACTTAAGGGA    2100

TAGTGTTGAT AGATAAATTA GAATGTATAG ATAGGTTTGT GAAAGTCTAA ATAATGGCTG    2160

TATAGATATG TATATATGGT TCACATATCT GGATCTGTGT ATTTGATTTT GTACTTTAAA    2220

TGTGACAAAT AAACCTTTTG GGAGAAAAAA AAAAAAARA AAAAAAAAAA AAAAAAAAA     2280

AAAAAAAAAA AAAAAAAAAA AAAAAAAAAA AAAAAAAAAA AAAAAAAAAA AAAAAAAAAA   2340

AAAAAAAAAA AAAAAAAAAA AAAAAAAAAA AAAAAAAAAA AAAAAAAAAA AAAAAAAAAA   2400

AAAAAAAAAA AAAAAAAAAA AAAAAAAAAA AAAAAAAAAA AAAAAAA                 2447
```

(2) INFORMATION FOR SEQ ID NO:15:

(i) SEQUENCE CHARACTERISTICS:
        (A) LENGTH: 335 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

```
Met Ala Thr Phe Val Ser Glu Leu Glu Ala Ala Lys Lys Asn Leu Ser
1               5                  10                  15

Glu Ala Leu Gly Asp Asn Val Lys Gln Tyr Trp Ala Asn Leu Lys Leu
            20                  25                  30

Trp Phe Lys Gln Lys Ile Ser Lys Glu Glu Phe Asp Leu Glu Ala His
        35                  40                  45

Arg Leu Leu Thr Gln Asp Asn Val His Ser His Asn Asp Phe Leu Leu
    50                  55                  60

Ala Ile Leu Thr Arg Cys Gln Ile Leu Leu Ser Thr Pro Asp Gly Ala
65                  70                  75                  80

Gly Ser Leu Pro Trp Pro Gly Gly Ser Ala Ala Lys Pro Gly Lys Pro
                85                  90                  95

Lys Gly Lys Lys Lys Leu Ser Ser Val Arg Gln Lys Phe Asp His Arg
            100                 105                 110
```

```
Phe Gln Pro Gln Asn Pro Leu Ser Gly Ala Gln Gln Phe Val Ala Lys
        115                 120                 125
Asp Pro Gln Asp Asp Asp Leu Lys Leu Cys Ser His Thr Met Met
130                 135                 140
Leu Pro Thr Arg Gly Gln Leu Glu Gly Arg Met Ile Val Thr Ala Tyr
145                 150                 155                 160
Glu His Gly Leu Asp Asn Val Thr Glu Glu Ala Val Ser Ala Val Val
                165                 170                 175
Tyr Ala Val Glu Asn His Leu Lys Asp Ile Leu Thr Ser Val Val Ser
                180                 185                 190
Arg Arg Lys Ala Tyr Arg Leu Arg Asp Gly His Phe Lys Tyr Ala Phe
        195                 200                 205
Gly Ser Asn Val Thr Pro Gln Pro Tyr Leu Lys Asn Ser Val Val Ala
        210                 215                 220
Tyr Asn Asn Leu Ile Glu Ser Pro Pro Ala Phe Thr Ala Pro Cys Ala
225                 230                 235                 240
Gly Gln Asn Pro Ala Ser His Pro Pro Asp Asp Ala Glu Gln Gln
                245                 250                 255
Ala Ala Leu Leu Leu Ala Cys Ser Gly Asp Thr Leu Pro Ala Ser Leu
                260                 265                 270
Pro Pro Val Asn Met Tyr Asp Leu Phe Glu Ala Leu Gln Val His Arg
        275                 280                 285
Glu Val Ile Pro Thr His Thr Val Tyr Ala Leu Asn Ile Glu Arg Ile
        290                 295                 300
Ile Thr Lys Leu Trp His Pro Asn His Glu Glu Leu Gln Gln Asp Lys
305                 310                 315                 320
Val His Arg Gln Arg Leu Ala Ala Lys Glu Gly Leu Leu Leu Cys
                325                 330                 335

(2) INFORMATION FOR SEQ ID NO:16:

(i) SEQUENCE CHARACTERISTICS:
        (A) LENGTH: 1622 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:16:

CTGACTTCCA CACCACTATG CAACCTTTCT GATATTCCTC CTGTTGGCAT AAAGAGCAAA      60

GCAGTTGTGG TTCCATGGGG AAGCTGCCAT TTTCTTGAAA AAGCCAGAAT TGCACAGAAA     120

GGAGGTGCTG AAGCAATGTT AGTTGTCAAT AACAGTGTCC TATTTCCTCC CTCAGGTAAC     180

AGATCTGAAT TCCTGATGT GAAAATACTG ATTGCATTTA TAAGCTACAA AGACTTTAGA     240

GATATGAACC AGACTCTAGG AGATAACATT ACTGTGAAAA TGTATTCTCC ATCGTGGCCT     300

AACTTTGATT ATACTATGGT GGTTATTTTT GTAATTGCGG TGTTCACTGT GGCATTAGGT     360

GGATACTGGA GTGGACTAGT TGAATTGGAA AACTTGAAAG CAGTGACAAC TGAAGATAGA     420

GAAATGAGGA AAAAGAAGGA AGAATATTTA ACTTTTAGTC CTCTTACAGT TGTAATATTT     480

GTGGTCATCT GCTGTGTTAT GATGGTCTTA CTTTATTTCT TCTACAAATG GTTGGTTTAT     540

GTTATGATAG CAATTTTCTG CATAGCATCA GCAATGAGTC TGTACAACTG TCTTGCTGCA     600

CTAATTCATA AGATACCATA TGGACAATGC ACGATTGCAT GTCGTGGCAA AAACATGGAA     660

GTGAGACTTA TTTTTCTCTC TGGACTGTGC ATAGCAGTAG CTGTTGTTTG GGCTGTGTTT     720
```

```
CGAAATGAAG ACAGGTGGGC TTGGATTTTA CAGGATATCT TGGGGATTGC TTTCTGTCTG      780

AATTTAATTA AAACACTGAA GTTGCCCAAC TTCAAGTCAT GTGTGATACT TCTAGGCCTT      840

CTCCTCCTCT ATGATGTATT TTTTGTTTTC ATAACACCAT TCATCACAAA GAATGGTGAG      900

AGTATCATGG TTGAACTCGC AGCTGGACCT TTTGGAAATA ATGAAAAGAA TGCCAGTAGT      960

CATCAGAGTA CCAAAACTGA TCTATTTCTC AGTAATGAGT GTGTGCCTCA TGCCTGTTTC     1020

AATATTGGGT TTTGGAGACA TTATTGTACC AGGCCTGTTG ATTGCATACT GTAGAAGATT     1080

TGATGTTCAG ACTGGTTCTT CTTACATATA CTATGTTTCG TCTACAGTTG CCTATGCTAT     1140

TGGCATGATA CTTACATTTG TTGTTCTGGT GCTGATGAAA AAGGGGCAAC CTGCTCTCCT     1200

CTATTTAGTA CCTTGCACAC TTATTACTGC CTCAGTTGTT GCCTGGGAGA CGTAAGGAAA     1260

TGGAAAAAGT TYTGGAAAGG TAACAGCTAT CAGATGATGG ACCATTTGGA TTGTGCAACA     1320

AATGAAGAAA ACCCTGTGAT ATYTGGTGAA CAGATTGTCC AGCAATAATA TTATGTGGAA     1380

CTGCTATAAT GTGTCATTGA TTTTYTACAA ATAGACTTCG ACTTTTTAAA TTGACTTTTG     1440

AATTGACAAT CTGAAAGAGT YTTCAATGAT ATGCTTGCAA AAATATATTT TTATGAGCTG     1500

GTACTGACAG TTACATCATA AATAACTAAA ACGCTTTGCT TTTAATGTTA AAGTTGTGCC     1560

TTCACATTAA ATAAAACATA TGGTCTGTGT AGTTTAAAAA AAAAAAAAAA AAAAAAAAA      1620

AA                                                                   1622

(2) INFORMATION FOR SEQ ID NO:17:

(i) SEQUENCE CHARACTERISTICS:
        (A) LENGTH: 312 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

Met Leu Val Val Asn Asn Ser Val Leu Phe Pro Pro Ser Gly Asn Arg
1               5                   10                  15

Ser Glu Phe Pro Asp Val Lys Ile Leu Ile Ala Phe Ile Ser Tyr Lys
            20                  25                  30

Asp Phe Arg Asp Met Asn Gln Thr Leu Gly Asp Asn Ile Thr Val Lys
        35                  40                  45

Met Tyr Ser Pro Ser Trp Pro Asn Phe Asp Tyr Thr Met Val Val Ile
    50                  55                  60

Phe Val Ile Ala Val Phe Thr Val Ala Leu Gly Gly Tyr Trp Ser Gly
65                  70                  75                  80

Leu Val Glu Leu Glu Asn Leu Lys Ala Val Thr Thr Glu Asp Arg Glu
                85                  90                  95

Met Arg Lys Lys Lys Glu Glu Tyr Leu Thr Phe Ser Pro Leu Thr Val
            100                 105                 110

Val Ile Phe Val Val Ile Cys Cys Val Met Met Val Leu Leu Tyr Phe
        115                 120                 125

Phe Tyr Lys Trp Leu Val Tyr Val Met Ile Ala Ile Phe Cys Ile Ala
    130                 135                 140

Ser Ala Met Ser Leu Tyr Asn Cys Leu Ala Ala Leu Ile His Lys Ile
145                 150                 155                 160

Pro Tyr Gly Gln Cys Thr Ile Ala Cys Arg Gly Lys Asn Met Glu Val
                165                 170                 175

Arg Leu Ile Phe Leu Ser Gly Leu Cys Ile Ala Val Ala Val Val Trp
            180                 185                 190
```

```
Ala Val Phe Arg Asn Glu Asp Arg Trp Ala Trp Ile Leu Gln Asp Ile
        195                 200                 205

Leu Gly Ile Ala Phe Cys Leu Asn Leu Ile Lys Thr Leu Lys Leu Pro
        210                 215                 220

Asn Phe Lys Ser Cys Val Ile Leu Leu Gly Leu Leu Leu Leu Tyr Asp
225                 230                 235                 240

Val Phe Phe Val Phe Ile Thr Pro Phe Ile Thr Lys Asn Gly Glu Ser
                245                 250                 255

Ile Met Val Glu Leu Ala Ala Gly Pro Phe Gly Asn Asn Glu Lys Asn
        260                 265                 270

Ala Ser Ser His Gln Ser Thr Lys Thr Asp Leu Phe Leu Ser Asn Glu
        275                 280                 285

Cys Val Pro His Ala Cys Phe Asn Ile Gly Phe Trp Arg His Tyr Cys
        290                 295                 300

Thr Arg Pro Val Asp Cys Ile Leu
305                 310

(2) INFORMATION FOR SEQ ID NO:18:

(i) SEQUENCE CHARACTERISTICS:
        (A) LENGTH: 1621 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:18:

CTCCGCTCCA GAGTTGAGCG CAGGTGAGCT CCTGCGCGTT CCGGGGGCGT TCCTCCAGTC      60

ACCCTCCCGC CGTTACCCGC GGCGCGCCCG AGGGAGTCTC CTCCAGACCC TCCCTCCCGT     120

TGCTCCAAAC TAATACGGAC TGAACGGATC GCTGCGAGGA TTATCTTACA CTGAACTGAT     180

CAAGTACTTT GAAAATGACT TCGAAATTTA TCTTGGTGTC CTTCATACTT GCTGCACTGA     240

GTCTTTCAAC CACCTTTTCT CTCCAACCAG ACCAGCAAAA GGTTCTACTA GTTTCTTTTG     300

ATGGATTCCG TTGGGATTAC TTATATAAAG TTCCAACGCC CCATTTTCAT TATATTATGA     360

AATATGGTGT TCACGTGAAG CAAGTTACTA ATGTTTTTAT TACAAAAACC TACCCTAACC     420

ATTATACTTT GGTAACTGGC CTCTTTGCAG AGAATCATGG GATTGTTGCA AATGATATGT     480

TTGATCCTAT TCGGAACAAA TCTTTCTCCT TGGATCACAT GAATATTTAT GATTCCAAGT     540

TTTGGGAAGA AGCGACACCA ATATGGATCA CAAACCAGAG GGCAGGACAT ACTAGTGGTG     600

CAGCCATGTG GCCCGGAACA GATGTAAAAA TACATAAGCG CTTTCCTACT CATTACATGC     660

CTTACAATGA GTCAGTTTCA TTTGAAGATA GAGTTGCCAA AATTGTTGAA TGGTTTACGT     720

CAAAAGAGCC CATAAATCTT GGTCTTCTCT ATTGGGAAGA CCCTGATGAC ATGGGCCACC     780

ATTTGGGACC TGACAGTCCG CTCATGGGGC CTGTCATTTC AGATATTGAC AAGAAGTTAG     840

GATATCTCAT ACAAATGCTG AAAAAGGCAA AGTTGTGGAA CACTCTGAAC CTAATCATCA     900

CAAGTGATCA TGGAATGACG CAGTGCTCTG AGGAAAGGTT AATAGAACTT GACCAGTACC     960

TGGATAAAGA CCACTATACC CTGATTGATC AATCTCCAGT AGCAGCCATC TTGCCAAAAG    1020

AAGGTAAATT TGATGAAGTT TATGAAGCAC TAACTCACGC TCATCCTAAT CTTACTGTTT    1080

ACAAAAAAGA AGACGTTCCA GAAAGGTGGC ATTACAAATA CAACAGTCGA ATTCAACCAA    1140

TCATAGCAGT GGCTGATGAA GGGTGGCACA TTTTACAGAA TAAGTCAGAT GACTTTCTGT    1200

ATGGCTGGAG TCAGCTGGCA AATACAGAAG CAGGAAACAT TACACTGAAG CTCAGAAAAT    1260
```

```
AATATCCCCA AATGAAGGCA TCAGAAATAA AAGTTCTTCT CTGACCTTCT TTCTCTCAAG    1320

ACATTGTATT ATGAAAAATT TCCAGCATAC AGAAAGTTG AAGAACACCC ACATGCCTGC     1380

TACTCAGATT CTACAATAAA CATTTGCTAT ATTTGTTTTA CCTACATATC TAGTCATCCA    1440

TCCATCCATT CATATTATTT TTAATGCACG TCTTATTTTT TAATGCACTG TCAACTACAG    1500

ACATCAGTAC TCTTCACCTC CAAACATTTC AGCAACATAT CATTAACGAT AGTCAAAAAT    1560

TTGTTTAGAG TTCCTTTTGT TTTAAATAAA ATTTATAAAG AAAAAAAAAA AAAAAAAAA     1620

A                                                                    1621
```

(2) INFORMATION FOR SEQ ID NO:19:

(i) SEQUENCE CHARACTERISTICS:
        (A) LENGTH: 355 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

```
Met Thr Ser Lys Phe Ile Leu Val Ser Phe Ile Leu Ala Ala Leu Ser
 1               5                  10                  15

Leu Ser Thr Thr Phe Ser Leu Gln Pro Asp Gln Gln Lys Val Leu Leu
                20                  25                  30

Val Ser Phe Asp Gly Phe Arg Trp Asp Tyr Leu Tyr Lys Val Pro Thr
            35                  40                  45

Pro His Phe His Tyr Ile Met Lys Tyr Gly Val His Val Lys Gln Val
        50                  55                  60

Thr Asn Val Phe Ile Thr Lys Thr Tyr Pro Asn His Tyr Thr Leu Val
65                  70                  75                  80

Thr Gly Leu Phe Ala Glu Asn His Gly Ile Val Ala Asn Asp Met Phe
                85                  90                  95

Asp Pro Ile Arg Asn Lys Ser Phe Ser Leu Asp His Met Asn Ile Tyr
            100                 105                 110

Asp Ser Lys Phe Trp Glu Glu Ala Thr Pro Ile Trp Ile Thr Asn Gln
        115                 120                 125

Arg Ala Gly His Thr Ser Gly Ala Ala Met Trp Pro Gly Thr Asp Val
    130                 135                 140

Lys Ile His Lys Arg Phe Pro Thr His Tyr Met Pro Tyr Asn Glu Ser
145                 150                 155                 160

Val Ser Phe Glu Asp Arg Val Ala Lys Ile Val Glu Trp Phe Thr Ser
                165                 170                 175

Lys Glu Pro Ile Asn Leu Gly Leu Leu Tyr Trp Glu Asp Pro Asp Asp
            180                 185                 190

Met Gly His His Leu Gly Pro Asp Ser Pro Leu Met Gly Pro Val Ile
        195                 200                 205

Ser Asp Ile Asp Lys Lys Leu Gly Tyr Leu Ile Gln Met Leu Lys Lys
    210                 215                 220

Ala Lys Leu Trp Asn Thr Leu Asn Leu Ile Ile Thr Ser Asp His Gly
225                 230                 235                 240

Met Thr Gln Cys Ser Glu Glu Arg Leu Ile Glu Leu Asp Gln Tyr Leu
                245                 250                 255

Asp Lys Asp His Tyr Thr Leu Ile Asp Gln Ser Pro Val Ala Ala Ile
            260                 265                 270

Leu Pro Lys Glu Gly Lys Phe Asp Glu Val Tyr Glu Ala Leu Thr His
        275                 280                 285
```

```
Ala His Pro Asn Leu Thr Val Tyr Lys Lys Glu Asp Val Pro Glu Arg
    290                 295                 300

Trp His Tyr Lys Tyr Asn Ser Arg Ile Gln Pro Ile Ile Ala Val Ala
305                 310                 315                 320

Asp Glu Gly Trp His Ile Leu Gln Asn Lys Ser Asp Asp Phe Leu Tyr
                325                 330                 335

Gly Trp Ser Gln Leu Ala Asn Thr Glu Ala Gly Asn Ile Thr Leu Lys
                340                 345                 350

Leu Arg Lys
        355
```

(2) INFORMATION FOR SEQ ID NO:20:

(i) SEQUENCE CHARACTERISTICS:
        (A) LENGTH: 3704 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:20:

```
CTCTAATCTC TGTCTGGATA CTTTTAGGAA AAGAACCTTG TTATTATGTA CTAAAGTGAA    60
TAATTTGTGC TCTTAGAGTA GGAGTTGGAA CTATAGGACT TGAAGGCAAG AGCAGGTATC   120
TTATCAAGGA TCTACTCACT CAGTTTCCCT AAAGCTCTCT CTCCAGATCG GATTCAACCG   180
CACATCATGA CAGATGTTCC GGCTACATTT ACCCAGGCTG AGTGTAATGG GGATAAACCA   240
CCTGAAAACG GTCAACAAAC AATCACTAAA ATCAGTGAGG AATTGACTGA TGTGGACAGC   300
CCCCTGCCAC ACTACAGGGT AGAACCCAGT CTGGAAGGTG CACTCACCAA AGGAAGTCAG   360
GAGGAAAGAA GAAAATTACA AGGGAACATG CTGCTCAACT CATCCATGGA GGACAAAATG   420
CTAAAAGAAA ACCCAGAAGA GAAACTCTTT ATTGTTCATA AGGCTATCAC AGATCTTTCT   480
CTCCAAGAAA CTAGTGCTGA TGAAATGACA TTCAGAGAAG GGCATCAGTG GGAGAAGATT   540
CCTCTGAGTG GCAGTAACCA GGAAATAAGA AGACAGAAGG AGAGGATTAC TGAGCAGCCT   600
CTCAAAGAGG AAGAAGATGA GGACAGGAAG AACAAAGGTC ACCAGGCAGC TGAAATTGAA   660
TGGCTGGGAT TTCGAAAACC TAGCCAAGCT GACATGTTAC ATTCTAAACA TGATGAGGAG   720
CAGAAGGTTT GGGATGAAGA AATTGATGAT GATGATGATG ATAATTGCAA TAATGATGAA   780
GATGAAGTTC GAGTGATAGA ATTTAAGAAA AAACATGAAG AGGTTTCTCA ATTTAAAGAG   840
GAAGGTGATG CAAGTGAGGA CTCCCCACTG AGCAGTGCCA GTTCCCAAGC TGTGACACCT   900
GATGAGCAGC CAACCTTAGG GAAGAAGAGT GATATCTCCA GAAATGCTTA TTCCAGATAC   960
AATACAATAT CCTATCGGAA AATCAGAAAG GGAAATACCA AGCAAAGAAT TGATGAATTC  1020
GAGTCTATGA TGCATTTATA AACTAACTGG AACTGAGAAA TTCTCATGCC CACTAAAGGA  1080
AAAGCTAATT CTATTGCCCC AGGGTGCATA TTTCTATGCC TTATTTGAGT TATCACTTGG  1140
AGGGAGGTGG AAGTTGACTC TCTTTTTCAC TGTAGAATAA TGTGGAAATA ACCCTAGATA  1200
AAAATTCAGT CTGATAACCT CAAATCAAAA AGCTTTAAAT AAATTCTTGG GCATTTATCT  1260
TTTAAAACTT CACTAATATA GCATTGTGTG ATAAGCACTA AGCAGTCAGT CCCCTGGGGG  1320
AATCTGGCAT AATTCGGCTA TAAATGTAGC AATGCTTGGA AAGGTAGTCA TCAAATGAGA  1380
CTATTTGAGG GGACTATTTG AAATGATTCT GGTATTTCTT TTGGTATCTT TCTTCCTGTA  1440
CATTGGAGTG ATGGAAAGTC TGGTATTAAA ACCTCTCTTA CTTTTAAACT TGATTTTGCA  1500
GACTCTGGCA ATAAGCCTTC CAAAATTCTG TGCCTTTTCT ATTATCACCA AACAATATGT  1560
```

```
TAAGTGGCTT TCCTTGGCAT CTACAGAGAA AACATTCTAT AGCCCTCCTT CCTAGGTGTT      1620

ACCATTCACT GAATCTTCTC TCAGAGGGAG ATGAGCAATT GTCAGTCAGG ATAATTCTGT      1680

TTGCTAAATG TTGCCTTTAT GCTTTCAAAC TGAATTAAAC CCATTGTGAG GTTGACACTG      1740

GGAGGGGCTA AAGATTGGT GGGCAGCAGA CTAAAGAGTT ATGTTGGATA GTTTTATTTC       1800

TGTGGCTGAA AATAAAATCT TGTCTAGCAC AGTTAAAGTC ATTAAAAATA AAATGACAG       1860

CTTTAGCACA ATTTTAAGAA AATGCCCCTC TCTATTACCA CATTTTCTCT TATTAACAGT     1920

ATCTCAGAAT AATTTTCTTT CCTTAGAAAC CTGAGAGAAT GCTAGTCATA ACTGTACTAG     1980

TTACTATGAA AATGGAAATA ATTATCTTAG AATATTTTCA AAGTAGAGCG TGAGCATGTA     2040

TTTTTAGTGG GAGAGCTCTG ATAGTTGTTG GGAATATATA ATTTACTGGA CCTCAGCCCA     2100

AATCAAGATG CTTAAAATTG TACTTGTGGA GCTTCACTCA AACCAATGTG TCAAATAACG     2160

TATTGAATAT TTATGAAAAG AGAGACTATA TTTATATTCT TAGATAGTTT GTTCCACAAT     2220

TTTTCATTTC ATGCTTCCAT ATATATTACC CTGAACTTTC TATCACCACA GATAAAGATT     2280

TTGTTTTGCC CTGCAAATAA AAAGACAATT CCTTATTGTC TGAATGTAAT ACAGTCTTCA     2340

TTGTACTATT CAACCCTTTG TTTCTTTCTT TTTCATTTTG TGAAAAACTC CATGTTAGTC     2400

CTCTTAGATG ACTGCTTATT TATGTGTAAC ATAAATCCCA CATATTCTAA TGACAACTTC     2460

TTTAATCCTT CCGGGTCATA TATTATATTT CCATAGTATC ACATACTATT ATTTAGTTGT     2520

TTACAAGACT CCAATTTGAA TTCAGGATTA CAGTGCTCCT TTCATTCTTT CAAACAGATA     2580

ACATAAAAGT TCTGTTACCC TCATTCTATA CAACCTATGG ATTTCATGTG TTACAATATC     2640

AGTTTCCAGA ATAAAGTGAG GGAAATCAGG TCTTTATTGA TAAAGTTAGG GAGAAGATTG     2700

ATGCAATAGG ACAATTTCCA ATTTAATTTA GATCCTCTAA TCTTTCTACA TGGACAAGCT     2760

GTTTTCTTTT CTAGGTTACT GATAACCCCT ACAATTTTCG ACTTAACTTC AAAACACAGT     2820

ATTGTGTTAT CTATCACATA ACAGGACCAT GTTTTTAACC TACCATCAAG AGCCTGTATT     2880

TTGAGTTATT CCAACAGAGA TGATGGATTC CTGTAGAACT AGAGGTGGGT GACCTATGGT     2940

TATGTGGCAC GGCAAAGCAA GTACCTCTTA AGGGACTCTA ATATATGCTA ACGCTGGTCC     3000

TCTTAGCTCT GTGCTCTCAC CAGACAATGA ATGAACTATG AAAGATTTAG TCAACAGAAA    3060

CTATTTTAGG GTATGTTTAG TTGGTAAATG CTTCATGTTC ATGGATGACA CAATGTTTTT    3120

GCAAAAAAAC CCTGAAACTA TTCTTTGGCA TTGGTGTCCA TGGCCCTATA CCGCCATCTT    3180

ACACGAAAGC CACAGAGTTG AAAGCCACAG AGTTGAAAGC CACAGAGTTA AGTGACCTCA    3240

GGTAACATAA TGGTGATGGT TGGCCATTTG AGTCTTTGTA ACCTAGGAAA GACAAAGGTC    3300

TGATTCAGAT TGCATGGGGG ATTTTTAACA TATTTGAAAC TCAGGGGAA CATGATTAAG     3360

AACACAAACT GGTAGCTACA CATGAAGGTT TACTTGAGCT TTTGTGATTC AAAGTTCAGG    3420

GGTGGTAAGG ACTCTGGTAC CAGGGAAGAG GGAGAATTAA TTTATTGTGC AAATGCTGGT   3480

ATTTCTTACA TGATTTTTTG TTTTCCTCTG TTGCTAGATA AATAGAAACT AATAATAGCT    3540

CTATTTCTCT GCCAATATAA AATCTACCTT TCATATAATG CTACATTGAA GGCACAGAAT   3600

TTGCTACCAT CTCTCTCTCC CCCTACCTAC CAAACTATCC ACAATTTAAA TAAAGAACTG   3660

CTGTGTCTGA CTTAAAAAAA AAAAAAAAAA AAAAAAAAA AAAA                     3704
```

(2) INFORMATION FOR SEQ ID NO:21:

(i) SEQUENCE CHARACTERISTICS:
        (A) LENGTH: 284 amino acids
        (B) TYPE: amino acid
        (C) STRANDEDNESS:

(D) TOPOLOGY: linear (ii) MOLECULE TYPE: protein (xi) SEQUENCE DESCRIPTION: SEQ ID NO:21:

Met Thr Asp Val Pro Ala Thr Phe Thr Gln Ala Glu Cys Asn Gly Asp
1               5                   10                  15

Lys Pro Pro Glu Asn Gly Gln Gln Thr Ile Thr Lys Ile Ser Glu Glu
                20                  25                  30

Leu Thr Asp Val Asp Ser Pro Leu Pro His Tyr Arg Val Glu Pro Ser
            35                  40                  45

Leu Glu Gly Ala Leu Thr Lys Gly Ser Gln Glu Glu Arg Arg Lys Leu
        50                  55                  60

Gln Gly Asn Met Leu Leu Asn Ser Ser Met Glu Asp Lys Met Leu Lys
65                  70                  75                  80

Glu Asn Pro Glu Glu Lys Leu Phe Ile Val His Lys Ala Ile Thr Asp
                85                  90                  95

Leu Ser Leu Gln Glu Thr Ser Ala Asp Glu Met Thr Phe Arg Glu Gly
            100                 105                 110

His Gln Trp Glu Lys Ile Pro Leu Ser Gly Ser Asn Gln Glu Ile Arg
        115                 120                 125

Arg Gln Lys Glu Arg Ile Thr Glu Gln Pro Leu Lys Glu Glu Glu Asp
130                 135                 140

Glu Asp Arg Lys Asn Lys Gly His Gln Ala Ala Glu Ile Glu Trp Leu
145                 150                 155                 160

Gly Phe Arg Lys Pro Ser Gln Ala Asp Met Leu His Ser Lys His Asp
                165                 170                 175

Glu Glu Gln Lys Val Trp Asp Glu Glu Ile Asp Asp Asp Asp Asp Asp
            180                 185                 190

Asn Cys Asn Asn Asp Glu Asp Glu Val Arg Val Ile Glu Phe Lys Lys
        195                 200                 205

Lys His Glu Glu Val Ser Gln Phe Lys Glu Glu Gly Asp Ala Ser Glu
    210                 215                 220

Asp Ser Pro Leu Ser Ser Ala Ser Ser Gln Ala Val Thr Pro Asp Glu
225                 230                 235                 240

Gln Pro Thr Leu Gly Lys Lys Ser Asp Ile Ser Arg Asn Ala Tyr Ser
                245                 250                 255

Arg Tyr Asn Thr Ile Ser Tyr Arg Lys Ile Arg Lys Gly Asn Thr Lys
            260                 265                 270

Gln Arg Ile Asp Glu Phe Glu Ser Met Met His Leu
        275                 280

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:22:

ANAAGCTTCCA TCAGTCAACC AAACCTCG                                   29

(2) INFORMATION FOR SEQ ID NO:23:

(i) SEQUENCE CHARACTERISTICS:

(A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:23:

ANGGATCTTCA TATCCACCAC GATAGTTA                                29

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:24:

ANAGGGACAGA ACCACCAAGT ACACAATG                                29

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:25:

ANGAGAAAGGG AGTGAGGGAA GTAGGAGG                                29

(2) INFORMATION FOR SEQ ID NO:26:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:26:

ANGTCGAATCA GGTCTTCCAT CGTAACAG                                29

(2) INFORMATION FOR SEQ ID NO:27:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:27:

GNCATCATTGC CCGAGGACTC GTAGCCTT                                29

(2) INFORMATION FOR SEQ ID NO:28:

(i) SEQUENCE CHARACTERISTICS:

```
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:28:

TNTCCTGTGTG AGAAGTCTAT GAGCTTCA                                       29

(2) INFORMATION FOR SEQ ID NO:29:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:29:

CNTATGAATTA GTGCAGCAAG ACAGTTGT                                       29

(2) INFORMATION FOR SEQ ID NO:30:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:30:

TNAGTGCAGCA AGTATGAAGG ACACCAAG                                       29

(2) INFORMATION FOR SEQ ID NO:31:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:31:

ANGTGCGGTTG AATCCGATCT GGAGAGAG                                       29

(2) INFORMATION FOR SEQ ID NO:32:

(i) SEQUENCE CHARACTERISTICS:
          (A) LENGTH: 81 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO:32:

Met Ser Ile Leu Thr Met Ile Ser Ser Trp Pro Phe Ser Arg Val Val
1               5                  10                  15

Arg Phe Cys Phe Leu His Gln Met Val Leu Asp Leu Cys Leu Gly Gln
            20                  25                  30

Gly Val Pro Gln Gln Asn Leu Glu Asn Pro Arg Glu Arg Lys Ser Phe
```

```
                          35                  40                  45
Leu Leu Phe Val Arg Asn Leu Ile Ile Asp Ser Ser Leu Lys Ile Leu
    50                      55                  60

Ser Gln Glu Pro Ser Asn Leu Trp Gln Arg Ile Pro Lys Met Met Thr
65                      70                  75                  80

Thr
```

SECRETED PROTEINS AND POLYNUCLEOTIDES ENCODING THEM

This application is a continuation-in-part of Ser. No. 60/080,233 (converted to a provisional application from non-provisional application Ser. No. 08/792,511), filed Jan. 31, 1997, which is incorporated by reference herein.

FIELD OF THE INVENTION

The present invention provides novel polynucleotides and proteins encoded by such polynucleotides, along with therapeutic, diagnostic and research utilities for these polynucleotides and proteins.

BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

SUMMARY OF THE INVENTION

In one embodiment, the present invention provides a composition comprising an isolated polynucleotide selected from the group consisting of:

(a) a polynucleotide comprising the nucleotide sequence of SEQ ID NO:1;
(b) a polynucleotide comprising the nucleotide sequence of SEQ ID NO:1 from nucleotide 374 to nucleotide 505;
(c) a polynucleotide comprising the nucleotide sequence of SEQ ID NO:1 from nucleotide 374 to nucleotide 518;
(d) a polynucleotide comprising the nucleotide sequence of the full-length protein coding sequence of clone AM973_1 deposited under accession number ATCC 98311;
(e) a polynucleotide encoding the full-length protein encoded by the cDNA insert of clone AM973_1 deposited under accession number ATCC 98311;
(f) a polynucleotide comprising the nucleotide sequence of the mature protein coding sequence of clone AM973_1 deposited under accession number ATCC 98311;
(g) a polynucleotide encoding the mature protein encoded by the cDNA insert of clone AM973_1 deposited under accession number ATCC 98311;
(h) a polynucleotide encoding a protein comprising the amino acid sequence of SEQ ID NO:2;
(i) a polynucleotide encoding a protein comprising a fragment of the amino acid sequence of SEQ ID NO:2 having biological activity;
(j) a polynucleotide which is an allelic variant of a polynucleotide of (a)–(g) above;
(k) a polynucleotide which encodes a species homologue of the protein of (h) or (i) above; and
(l) a polynucleotide capable of hybridizing under stringent conditions to any one of the polynucleotides specified in (a)–(i).

Preferably, such polynucleotide comprises the nucleotide sequence of SEQ ID NO:1 from nucleotide 374 to nucleotide 505; the nucleotide sequence of SEQ ID NO:1 from nucleotide 374 to nucleotide 518; the nucleotide sequence of the full-length protein coding sequence of clone AM973_1 deposited under accession number ATCC 98311; or the nucleotide sequence of the mature protein coding sequence of clone AM973_1 deposited under accession number ATCC 98311. In other preferred embodiments, the polynucleotide encodes the full-length or mature protein encoded by the cDNA insert of clone AM973_1 deposited under accession number ATCC 98311.

Other embodiments provide the gene corresponding to the cDNA sequence of SEQ ID NO:1.

In other embodiments, the present invention provides a composition comprising a protein, wherein said protein comprises an amino acid sequence selected from the group consisting of:

(a) the amino acid sequence of SEQ ID NO:2;
(b) fragments of the amino acid sequence of SEQ ID NO:2; and
(c) the amino acid sequence encoded by the cDNA insert of clone AM973_1 deposited under accession number ATCC 98311;

the protein being substantially free from other mammalian proteins. Preferably such protein comprises the amino acid sequence of SEQ ID NO:2.

In one embodiment, the present invention provides a composition comprising an isolated polynucleotide selected from the group consisting of:

(a) a polynucleotide comprising the nucleotide sequence of SEQ ID NO:3;
(b) a polynucleotide comprising the nucleotide sequence of SEQ ID NO:3 from nucleotide 43 to nucleotide 384;
(c) a polynucleotide comprising the nucleotide sequence of the full-length protein coding sequence of clone BK260_2 deposited under accession number ATCC 98311;
(d) a polynucleotide encoding the full-length protein encoded by the cDNA insert of clone BK260_2 deposited under accession number ATCC 98311;
(e) a polynucleotide comprising the nucleotide sequence of the mature protein coding sequence of clone BK260_2 deposited under accession number ATCC 98311;
(f) a polynucleotide encoding the mature protein encoded by the cDNA insert of clone BK260_2 deposited under accession number ATCC 98311;
(g) a polynucleotide encoding a protein comprising the amino acid sequence of SEQ ID NO:4;
(h) a polynucleotide encoding a protein comprising a fragment of the amino acid sequence of SEQ ID NO:4 having biological activity;
(i) a polynucleotide which is an allelic variant of a polynucleotide of (a)–(f) above;

(j) a polynucleotide which encodes a species homologue of the protein of (g) or (h) above; and (k) a polynucleotide capable of hybridizing under stringent conditions to any one of the polynucleotides specified in (a)–(h).

Preferably, such polynucleotide comprises the nucleotide sequence of SEQ ID NO:3 from nucleotide 43 to nucleotide 384; the nucleotide sequence of the full-length protein coding sequence of clone BK260_2 deposited under accession number ATCC 98311; or the nucleotide sequence of the mature protein coding sequence of clone BK260_2 deposited under accession number ATCC 98311. In other preferred embodiments, the polynucleotide encodes the full-length or mature protein encoded by the cDNA insert of clone BK260_2 deposited under accession number ATCC 98311. In yet other preferred embodiments, the present invention provides a polynucleotide encoding a protein comprising the amino acid sequence of SEQ ID NO:4 from amino acid 27 to amino acid 114.

Other embodiments provide the gene corresponding to the cDNA sequence of SEQ ID NO:3 or SEQ ID NO:5.

In other embodiments, the present invention provides a composition comprising a protein, wherein said protein comprises an amino acid sequence selected from the group consisting of:

(a) the amino acid sequence of SEQ ID NO:4;
(b) the amino acid sequence of SEQ ID NO:4 from amino acid 27 to amino acid 114;
(c) fragments of the amino acid sequence of SEQ ID NO:4; and
(d) the amino acid sequence encoded by the cDNA insert of clone BK260_2 deposited under accession number ATCC 98311;

the protein being substantially free from other mammalian proteins. Preferably such protein comprises the amino acid sequence of SEQ ID NO:4 or the amino acid sequence of SEQ ID NO:4 from amino acid 27 to amino acid 114.

In one embodiment, the present invention provides a composition comprising an isolated polynucleotide selected from the group consisting of:

(a) a polynucleotide comprising the nucleotide sequence of SEQ ID NO:6;
(b) a polynucleotide comprising the nucleotide sequence of SEQ ID NO:6 from nucleotide 158 to nucleotide 418;
(c) a polynucleotide comprising the nucleotide sequence of SEQ ID NO:6 from nucleotide 353 to nucleotide 418;
(d) a polynucleotide comprising the nucleotide sequence of SEQ ID NO:6 from nucleotide 1 to nucleotide 397;
(e) a polynucleotide comprising the nucleotide sequence of the full-length protein coding sequence of clone BR390_1 deposited under accession number ATCC 98311;
(f) a polynucleotide encoding the full-length protein encoded by the cDNA insert of clone BR390_1 deposited under accession number ATCC 98311;
(g) a polynucleotide comprising the nucleotide sequence of the mature protein coding sequence of clone BR390_1 deposited under accession number ATCC 98311;
(h) a polynucleotide encoding the mature protein encoded by the cDNA insert of clone BR390_1 deposited under accession number ATCC 98311;
(i) a polynucleotide encoding a protein comprising the amino acid sequence of SEQ ID NO:7;
(j) a polynucleotide encoding a protein comprising a fragment of the amino acid sequence of SEQ ID NO:7 having biological activity;
(k) a polynucleotide which is an allelic variant of a polynucleotide of (a)–(h) above;
(l) a polynucleotide which encodes a species homologue of the protein of (i) or (j) above; and
(m) a polynucleotide capable of hybridizing under stringent conditions to any one of the polynucleotides specified in (a)–(j).

Preferably, such polynucleotide comprises the nucleotide sequence of SEQ ID NO:6 from nucleotide 158 to nucleotide 418; the nucleotide sequence of SEQ ID NO:6 from nucleotide 353 to nucleotide 418; the nucleotide sequence of SEQ ID NO:6 from nucleotide 1 to nucleotide 397; the nucleotide sequence of the full-length protein coding sequence of clone BR390_1 deposited under accession number ATCC 98311; or the nucleotide sequence of the mature protein coding sequence of clone BR390_1 deposited under accession number ATCC 98311. In other preferred embodiments, the polynucleotide encodes the full-length or mature protein encoded by the cDNA insert of clone BR390_1 deposited under accession number ATCC 98311. In yet other preferred embodiments, the present invention provides a polynucleotide encoding a protein comprising the amino acid sequence of SEQ ID NO:7 from amino acid 1 to amino acid 80.

Other embodiments provide the gene corresponding to the cDNA sequence of SEQ ID NO:6.

In other embodiments, the present invention provides a composition comprising a protein, wherein said protein comprises an amino acid sequence selected from the group consisting of:

(a) the amino acid sequence of SEQ ID NO:7;
(b) the amino acid sequence of SEQ ID NO:7 from amino acid 1 to amino acid 80;
(c) fragments of the amino acid sequence of SEQ ID NO:7; and
(d) the amino acid sequence encoded by the cDNA insert of clone BR390_1 deposited under accession number ATCC 98311;

the protein being substantially free from other mammalian proteins. Preferably such protein comprises the amino acid sequence of SEQ ID NO:7 or the amino acid sequence of SEQ ID NO:7 from amino acid 1 to amino acid 80.

In one embodiment, the present invention provides a composition comprising an isolated polynucleotide selected from the group consisting of:

(a) a polynucleotide comprising the nucleotide sequence of SEQ ID NO:8;
(b) a polynucleotide comprising the nucleotide sequence of SEQ ID NO:8 from nucleotide 424 to nucleotide 1785;
(c) a polynucleotide comprising the nucleotide sequence of SEQ ID NO:8 from nucleotide 805 to nucleotide 1785;
(d) a polynucleotide comprising the nucleotide sequence of SEQ ID NO:8 from nucleotide 1670 to nucleotide 2006;
(e) a polynucleotide comprising the nucleotide sequence of the full-length protein coding sequence of clone CJ539_3 deposited under accession number ATCC 98311;
(f) a polynucleotide encoding the full-length protein encoded by the cDNA insert of clone CJ539_3 deposited under accession number ATCC 98311;

(g) a polynucleotide comprising the nucleotide sequence of the mature protein coding sequence of clone CJ539_3 deposited under accession number ATCC 98311;

(h) a polynucleotide encoding the mature protein encoded by the cDNA insert of clone CJ539_3 deposited under accession number ATCC 98311;

(i) a polynucleotide encoding a protein comprising the amino acid sequence of SEQ ID NO:9;

(j) a polynucleotide encoding a protein comprising a fragment of the amino acid sequence of SEQ ID NO:9 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID NO:8 from nucleotide 424 to nucleotide 1785; the nucleotide sequence of SEQ ID NO:8 from nucleotide 805 to nucleotide 1785; the nucleotide sequence of SEQ ID NO:8 from nucleotide 1670 to nucleotide 2006; the nucleotide sequence of the full-length protein coding sequence of clone CJ539_3 deposited under accession number ATCC 98311; or the nucleotide sequence of the mature protein coding sequence of clone CJ539_3 deposited under accession number ATCC 98311. In other preferred embodiments, the polynucleotide encodes the full-length or mature protein encoded by the cDNA insert of clone CJ539_3 deposited under accession number ATCC 98311.

Other embodiments provide the gene corresponding to the cDNA sequence of SEQ ID NO:8.

In other embodiments, the present invention provides a composition comprising a protein, wherein said protein comprises an amino acid sequence selected from the group consisting of:

(a) the amino acid sequence of SEQ ID NO:9;

(b) fragments of the amino acid sequence of SEQ ID NO:9; and (c) the amino acid sequence encoded by the cDNA insert of clone CJ539_3 deposited under accession number ATCC 98311;

the protein being substantially free from other mammalian proteins. Preferably such protein comprises the amino acid sequence of SEQ ID NO:9.

In one embodiment, the present invention provides a composition comprising an isolated polynucleotide selected from the group consisting of:

(a) a polynucleotide comprising the nucleotide sequence of SEQ ID NO:10;

(b) a polynucleotide comprising the nucleotide sequence of SEQ ID NO:10 from nucleotide 156 to nucleotide 2060;

(c) a polynucleotide comprising the nucleotide sequence of SEQ ID NO:10 from nucleotide 285 to nucleotide 2060;

(d) a polynucleotide comprising the nucleotide sequence of SEQ ID NO:10 from nucleotide 940 to nucleotide 1667;

(e) a polynucleotide comprising the nucleotide sequence of the full-length protein coding sequence of clone CN729_3 deposited under accession number ATCC 98311;

(f) a polynucleotide encoding the full-length protein encoded by the cDNA insert of clone CN729_3 deposited under accession number ATCC 98311;

(g) a polynucleotide comprising the nucleotide sequence of the mature protein coding sequence of clone CN729_3 deposited under accession number ATCC 98311;

(h) a polynucleotide encoding the mature protein encoded by the cDNA insert of clone CN729_3 deposited under accession number ATCC 98311;

(i) a polynucleotide encoding a protein comprising the amino acid sequence of SEQ ID NO:11;

(j) a polynucleotide encoding a protein comprising a fragment of the amino acid sequence of SEQ ID NO:11 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID NO:10 from nucleotide 156 to nucleotide 2060; the nucleotide sequence of SEQ ID NO:10 from nucleotide 285 to nucleotide 2060; the nucleotide sequence of SEQ ID NO:10 from nucleotide 940 to nucleotide 1667; the nucleotide sequence of the full-length protein coding sequence of clone CN729_3 deposited under accession number ATCC 98311; or the nucleotide sequence of the mature protein coding sequence of clone CN729_3 deposited under accession number ATCC 98311. In other preferred embodiments, the polynucleotide encodes the full-length or mature protein encoded by the cDNA insert of clone CN729_3 deposited under accession number ATCC 98311. In yet other preferred embodiments, the present invention provides a polynucleotide encoding a protein comprising the amino acid sequence of SEQ ID NO:11 from amino acid 342 to amino acid 504.

Other embodiments provide the gene corresponding to the cDNA sequence of SEQ ID NO:10.

In other embodiments, the present invention provides a composition comprising a protein, wherein said protein comprises an amino acid sequence selected from the group consisting of:

(a) the amino acid sequence of SEQ ID NO:11;

(b) the amino acid sequence of SEQ ID NO:11 from amino acid 342 to amino acid 504;

(c) fragments of the amino acid sequence of SEQ ID NO:11; and (d) the amino acid sequence encoded by the cDNA insert of clone CN729_3 deposited under accession number ATCC 98311;

the protein being substantially free from other mammalian proteins. Preferably such protein comprises the amino acid sequence of SEQ ID NO:11 or the amino acid sequence of SEQ ID NO:11 from amino acid 342 to amino acid 504.

In one embodiment, the present invention provides a composition comprising an isolated polynucleotide selected from the group consisting of:

(a) a polynucleotide comprising the nucleotide sequence of SEQ ID NO:12;

(b) a polynucleotide comprising the nucleotide sequence of SEQ ID NO:12 from nucleotide 6 to nucleotide 1229;

(c) a polynucleotide comprising the nucleotide sequence of SEQ ID NO:12 from nucleotide 1 to nucleotide 784;

(d) a polynucleotide comprising the nucleotide sequence of the full-length protein coding sequence of clone CO139_3 deposited under accession number ATCC 98311;

(e) a polynucleotide encoding the full-length protein encoded by the cDNA insert of clone CO139_3 deposited under accession number ATCC 98311;

(f) a polynucleotide comprising the nucleotide sequence of the mature protein coding sequence of clone CO139_3 deposited under accession number ATCC 98311;

(g) a polynucleotide encoding the mature protein encoded by the cDNA insert of clone CO139_3 deposited under accession number ATCC 98311;

(h) a polynucleotide encoding a protein comprising the amino acid sequence of SEQ ID NO:13;

(i) a polynucleotide encoding a protein comprising a fragment of the amino acid sequence of SEQ ID NO:13 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:12 from nucleotide 6 to nucleotide 1229; the nucleotide sequence of SEQ ID NO:12 from nucleotide 1 to nucleotide 784; the nucleotide sequence of the full-length protein coding sequence of clone CO139_3 deposited under accession number ATCC 98311; or the nucleotide sequence of the mature protein coding sequence of clone CO139_3 deposited under accession number ATCC 98311. In other preferred embodiments, the polynucleotide encodes the full-length or mature protein encoded by the cDNA insert of clone CO139_3 deposited under accession number ATCC 98311. In yet other preferred embodiments, the present invention provides a polynucleotide encoding a protein comprising the amino acid sequence of SEQ ID NO:13 from amino acid 1 to amino acid 259.

Other embodiments provide the gene corresponding to the cDNA sequence of SEQ ID NO:12.

In other embodiments, the present invention provides a composition comprising a protein, wherein said protein comprises an amino acid sequence selected from the group consisting of:

(a) the amino acid sequence of SEQ ID NO:13;

(b) the amino acid sequence of SEQ ID NO:13 from amino acid 1 to amino acid 259;

(c) fragments of the amino acid sequence of SEQ ID NO:13; and (d) the amino acid sequence encoded by the cDNA insert of clone CO139_3 deposited under accession number ATCC 98311;

the protein being substantially free from other mammalian proteins. Preferably such protein comprises the amino acid sequence of SEQ ID NO:13 or the amino acid sequence of SEQ ID NO:13 from amino acid 1 to amino acid 259.

In one embodiment, the present invention provides a composition comprising an isolated polynucleotide selected from the group consisting of:

(a) a polynucleotide comprising the nucleotide sequence of SEQ ID NO:14;

(b) a polynucleotide comprising the nucleotide sequence of SEQ ID NO:14 from nucleotide 184 to nucleotide 1188;

(c) a polynucleotide comprising the nucleotide sequence of SEQ ID NO:14 from nucleotide 991 to nucleotide 1188;

(d) a polynucleotide comprising the nucleotide sequence of SEQ ID NO:14 from nucleotide 1 to nucleotide 402;

(e) a polynucleotide comprising the nucleotide sequence of the full-length protein coding sequence of clone CO1020_1 deposited under accession number ATCC 98311;

(f) a polynucleotide encoding the full-length protein encoded by the cDNA insert of clone CO1020_1 deposited under accession number ATCC 98311;

(g) a polynucleotide comprising the nucleotide sequence of the mature protein coding sequence of clone CO1020_1 deposited under accession number ATCC 98311;

(h) a polynucleotide encoding the mature protein encoded by the cDNA insert of clone CO1020_1 deposited under accession number ATCC 98311;

(i) a polynucleotide encoding a protein comprising the amino acid sequence of SEQ ID NO:15;

(j) a polynucleotide encoding a protein comprising a fragment of the amino acid sequence of SEQ ID NO:15 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID NO:14 from nucleotide 184 to nucleotide 1188; the nucleotide sequence of SEQ ID NO:14 from nucleotide 991 to nucleotide 1188; the nucleotide sequence of SEQ ID NO:14 from nucleotide 1 to nucleotide 402; the nucleotide sequence of the full-length protein coding sequence of clone CO1020_1 deposited under accession number ATCC 98311; or the nucleotide sequence of the mature protein coding sequence of clone CO1020_1 deposited under accession number ATCC 98311. In other preferred embodiments, the polynucleotide encodes the full-length or mature protein encoded by the cDNA insert of clone CO1020_1 deposited under accession number ATCC 98311.

Other embodiments provide the gene corresponding to the cDNA sequence of SEQ ID NO:14.

In other embodiments, the present invention provides a composition comprising a protein, wherein said protein comprises an amino acid sequence selected from the group consisting of:

(a) the amino acid sequence of SEQ ID NO:15;

(b) fragments of the amino acid sequence of SEQ ID NO:15; and (c) the amino acid sequence encoded by the cDNA insert of clone CO1020_1 deposited under accession number ATCC 98311;

the protein being substantially free from other mammalian proteins. Preferably such protein comprises the amino acid sequence of SEQ ID NO:15.

In one embodiment, the present invention provides a composition comprising an isolated polynucleotide selected from the group consisting of:

(a) a polynucleotide comprising the nucleotide sequence of SEQ ID NO:16;

(b) a polynucleotide comprising the nucleotide sequence of SEQ ID NO:16 from nucleotide 136 to nucleotide 1071;

(c) a polynucleotide comprising the nucleotide sequence of SEQ ID NO:16 from nucleotide 361 to nucleotide 1071;

(d) a polynucleotide comprising the nucleotide sequence of SEQ ID NO:16 from nucleotide 1 to nucleotide 951;

(e) a polynucleotide comprising the nucleotide sequence of the full-length protein coding sequence of clone CS752_3 deposited under accession number ATCC 98311;

(f) a polynucleotide encoding the full-length protein encoded by the cDNA insert of clone CS752_3 deposited under accession number ATCC 98311;

(g) a polynucleotide comprising the nucleotide sequence of the mature protein coding sequence of clone CS752_3 deposited under accession number ATCC 98311;

(h) a polynucleotide encoding the mature protein encoded by the cDNA insert of clone CS752_3 deposited under accession number ATCC 98311;

(i) a polynucleotide encoding a protein comprising the amino acid sequence of SEQ ID NO:17;

(j) a polynucleotide encoding a protein comprising a fragment of the amino acid sequence of SEQ ID NO:17 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID NO:16 from nucleotide 136 to nucleotide 1071; the nucleotide sequence of SEQ ID NO:16 from nucleotide 361 to nucleotide 1071; the nucleotide sequence of SEQ ID NO:16 from nucleotide 1 to nucleotide 951; the nucleotide sequence of the full-length protein coding sequence of clone CS752_3 deposited under accession number ATCC 98311; or the nucleotide sequence of the mature protein coding sequence of clone CS752_3 deposited under accession number ATCC 98311. In other preferred embodiments, the polynucleotide encodes the full-length or mature protein encoded by the cDNA insert of clone CS752_3 deposited under accession number ATCC 98311. In yet other preferred embodiments, the present invention provides a polynucleotide encoding a protein comprising the amino acid sequence of SEQ ID NO:17 from amino acid 1 to amino acid 272.

Other embodiments provide the gene corresponding to the cDNA sequence of SEQ ID NO:16.

In other embodiments, the present invention provides a composition comprising a protein, wherein said protein comprises an amino acid sequence selected from the group consisting of:

(a) the amino acid sequence of SEQ ID NO:17;

(b) the amino acid sequence of SEQ ID NO:17 from amino acid 1 to amino acid 272;

(c) fragments of the amino acid sequence of SEQ ID NO:17; and (d) the amino acid sequence encoded by the cDNA insert of clone CS752_3 deposited under accession number ATCC 98311;

the protein being substantially free from other mammalian proteins. Preferably such protein comprises the amino acid sequence of SEQ ID NO:17 or the amino acid sequence of SEQ ID NO:17 from amino acid 1 to amino acid 272.

In one embodiment, the present invention provides a composition comprising an isolated polynucleotide selected from the group consisting of:

(a) a polynucleotide comprising the nucleotide sequence of SEQ ID NO:18;

(b) a polynucleotide comprising the nucleotide sequence of SEQ ID NO:18 from nucleotide 195 to nucleotide 1259;

(c) a polynucleotide comprising the nucleotide sequence of SEQ ID NO:18 from nucleotide 261 to nucleotide 1259;

(d) a polynucleotide comprising the nucleotide sequence of SEQ ID NO:18 from nucleotide 1 to nucleotide 578;

(e) a polynucleotide comprising the nucleotide sequence of the full-length protein coding sequence of clone DM340_1 deposited under accession number ATCC 98311;

(f) a polynucleotide encoding the full-length protein encoded by the cDNA insert of clone DM340_1 deposited under accession number ATCC 98311;

(g) a polynucleotide comprising the nucleotide sequence of the mature protein coding sequence of clone DM340_1 deposited under accession number ATCC 98311;

(h) a polynucleotide encoding the mature protein encoded by the cDNA insert of clone DM340_1 deposited under accession number ATCC 98311;

(i) a polynucleotide encoding a protein comprising the amino acid sequence of SEQ ID NO:19;

(j) a polynucleotide encoding a protein comprising a fragment of the amino acid sequence of SEQ ID NO:19 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID from nucleotide 195 to nucleotide 1259; the nucleotide sequence of SEQ ID NO:18 from nucleotide 261 to nucleotide 1259; the nucleotide sequence of SEQ ID NO:18 from nucleotide 1 to nucleotide 578; the nucleotide sequence of the full-length protein coding sequence of clone DM340_1 deposited under accession number ATCC 98311; or the nucleotide sequence of the mature protein coding sequence of clone DM340_1 deposited under accession number ATCC 98311. In other preferred embodiments, the polynucleotide encodes the full-length or mature protein encoded by the cDNA insert of clone DM340_1 deposited under accession number ATCC 98311. In yet other preferred embodiments, the present invention provides a polynucleotide encoding a protein comprising the amino acid sequence of SEQ ID NO:19 from amino acid 1 to amino acid 128.

Other embodiments provide the gene corresponding to the cDNA sequence of SEQ ID NO:18.

In other embodiments, the present invention provides a composition comprising a protein, wherein said protein comprises an amino acid sequence selected from the group consisting of:

(a) the amino acid sequence of SEQ ID NO:19;

(b) the amino acid sequence of SEQ ID NO:19 from amino acid 1 to amino acid 128;

(c) fragments of the amino acid sequence of SEQ ID NO:19; and (d) the amino acid sequence encoded by the cDNA insert of clone DM340_1 deposited under accession number ATCC 98311;

the protein being substantially free from other mammalian proteins. Preferably such protein comprises the amino acid sequence of SEQ ID NO:19 or the amino acid sequence of SEQ ID NO:19 from amino acid 1 to amino acid 128.

In one embodiment, the present invention provides a composition comprising an isolated polynucleotide selected from the group consisting of:

(a) a polynucleotide comprising the nucleotide sequence of SEQ ID NO:20;

(b) a polynucleotide comprising the nucleotide sequence of SEQ ID NO:20 from nucleotide 187 to nucleotide 1038;

(c) a polynucleotide comprising the nucleotide sequence of SEQ ID NO:20 from nucleotide 1 to nucleotide 381;

(d) a polynucleotide comprising the nucleotide sequence of the full-length protein coding sequence of clone DW902 1 deposited under accession number ATCC 98311;

(e) a polynucleotide encoding the full-length protein encoded by the cDNA insert of clone DW902_1 deposited under accession number ATCC 98311;

(f) a polynucleotide comprising the nucleotide sequence of the mature protein coding sequence of clone DW902_1 deposited under accession number ATCC 98311;

(g) a polynucleotide encoding the mature protein encoded by the cDNA insert of clone DW902_1 deposited under accession number ATCC 98311;

(h) a polynucleotide encoding a protein comprising the amino acid sequence of SEQ ID NO:21;

(i) a polynucleotide encoding a protein comprising a fragment of the amino acid sequence of SEQ ID NO:21 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:20 from nucleotide 187 to nucleotide 1038; the nucleotide sequence of SEQ ID NO:20 from nucleotide 1 to nucleotide 381; the nucleotide sequence of the full-length protein coding sequence of clone DW902_1 deposited under accession number ATCC 98311; or the nucleotide sequence of the mature protein coding sequence of clone DW902_1 deposited under accession number ATCC 98311. In other preferred embodiments, the polynucleotide encodes the full-length or mature protein encoded by the cDNA insert of clone DW902_1 deposited under accession number ATCC 98311. In yet other preferred embodiments, the present invention provides a polynucleotide encoding a protein comprising the amino acid sequence of SEQ ID NO:21 from amino acid 1 to amino acid 65.

Other embodiments provide the gene corresponding to the cDNA sequence of SEQ ID NO:20.

In other embodiments, the present invention provides a composition comprising a protein, wherein said protein comprises an amino acid sequence selected from the group consisting of:

(a) the amino acid sequence of SEQ ID NO:21;

(b) the amino acid sequence of SEQ ID NO:21 from amino acid 1 to amino acid 65;

(c) fragments of the amino acid sequence of SEQ ID NO:21; and (d) the amino acid sequence encoded by the cDNA insert of clone DW902_1 deposited under accession number ATCC 98311;

the protein being substantially free from other mammalian proteins. Preferably such protein comprises the amino acid sequence of SEQ ID NO:21 or the amino acid sequence of SEQ ID NO:21 from amino acid 1 to amino acid 65.

In certain preferred embodiments, the polynucleotide is operably linked to an expression control sequence. The invention also provides a host cell, including bacterial, yeast, insect and mammalian cells, transformed with such polynucleotide compositions. Also provided by the present invention are organisms that have enhanced, reduced, or modified expression of the gene(s) corresponding to the polynucleotide sequences disclosed herein.

Processes are also provided for producing a protein, which comprise:

(a) growing a culture of the host cell transformed with such polynucleotide compositions in a suitable culture medium; and (b) purifying the protein from the culture.

The protein produced according to such methods is also provided by the present invention. Preferred embodiments include those in which the protein produced by such process is a mature form of the protein.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

Figure 1A:
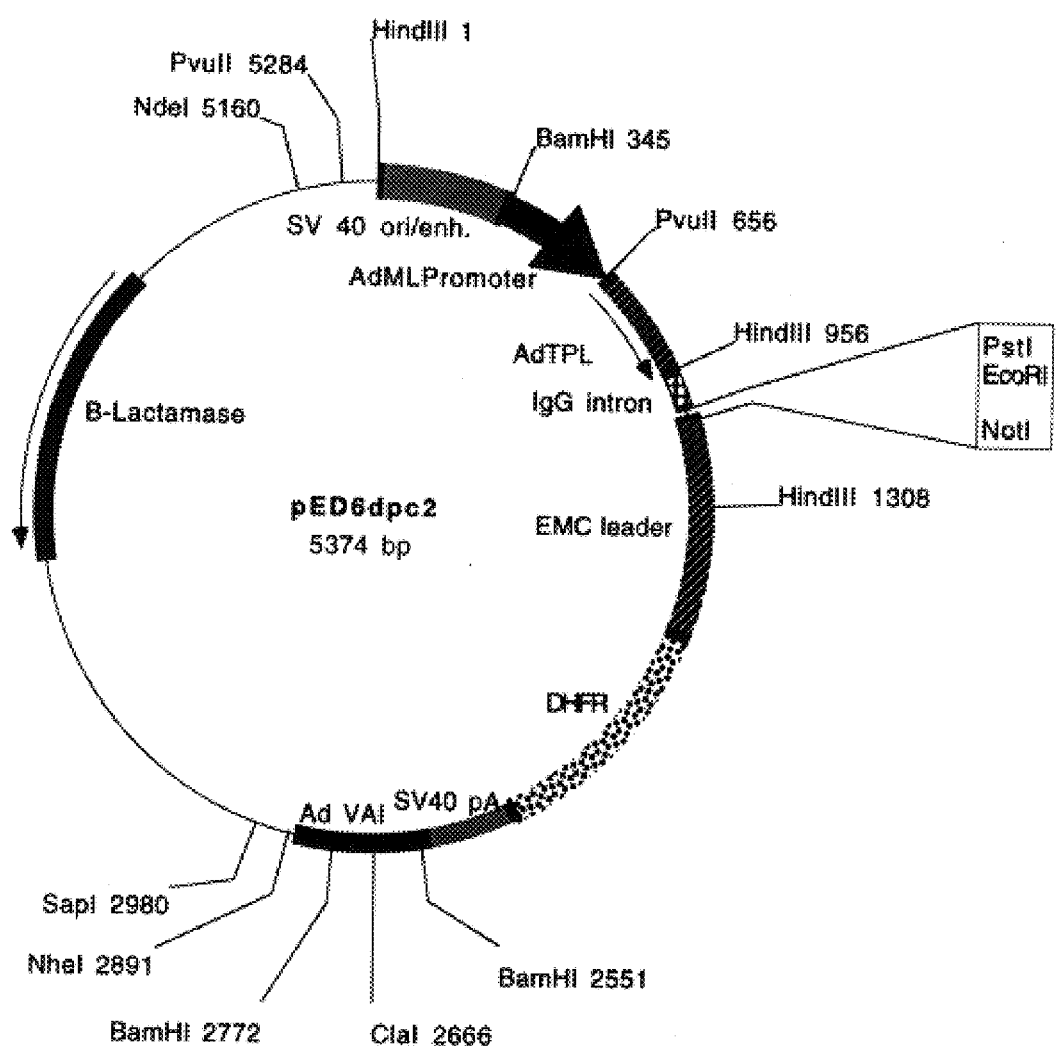
FIGS. 1A and 1B are schematic representations of the pED6 and pNOTs vectors, respectively, used for deposit of clones disclosed herein.

DETAILED DESCRIPTION
ISOLATED PROTEINS AND POLYNUCLEOTIDES

Nucleotide and amino acid sequences, as presently determined, are reported below for each clone and protein disclosed in the present application. The nucleotide sequence of each clone can readily be determined by sequencing of the deposited clone in accordance with known methods. The predicted amino acid sequence (both full-length and mature) can then be determined from such nucleotide sequence. The amino acid sequence of the protein encoded by a particular clone can also be determined by expression of the clone in a suitable host cell, collecting the protein and determining its sequence. For each disclosed protein applicants have identified what they have determined to be the reading frame best identifiable with sequence information available at the time of filing.

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Clone "AM973 1"

A polynucleotide of the present invention has been identified as clone "AM973_1". AM973_1 was isolated from a human fetal kidney cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. AM973_1 is a full-length clone, including the entire coding sequence of a secreted protein (also referred to herein as "AM973_1 protein").

The nucleotide sequence of AM973_1 as presently determined is reported in SEQ ID NO:1. What applicants presently believe to be a possible reading frame and predicted amino acid sequence of the AM973_1 protein corresponding to the foregoing nucleotide sequence is reported in SEQ ID NO:2; this reading frame would be transcribed from the complementary DNA strand to that shown in SEQ ID NO:1 starting at nucleotide 505 and ending at nucleotide 374 of SEQ ID NO:1.

The EcoRI/NotI restriction fragment obtainable from the deposit containing clone AM973_1 should be approximately 3300 bp.

The nucleotide sequence disclosed herein for AM973_1 was searched against the GenBank and GeneSeq nucleotide sequence databases using BLASTN/BLASTX and FASTA search protocols. AM973_1 demonstrated at least some similarity with sequences identified as N68677 (za21g03.s1 Homo sapiens cDNA clone 293236 3' similar to contains Alu repetitive element), X92185 (H.sapiens mRNA for alu elements), and Z68756 (Human DNA sequence from cosmid L191F1, Huntington's Disease Region, chromosome 4p16.3 contains Huntington Disease (HD) gene, CpG island ESTs and U7 small nuclear RNA). The predicted amino acid sequence disclosed herein for AM973_1 was searched against the GenPept and GeneSeq amino acid sequence databases using the BLASTX search protocol. The predicted AM973_1 protein demonstrated at least some similarity to sequences identified as S58722 (X-linked retinopathy protein {C-terminal, clone XEH.8c} [human, Peptide Partial, 100 aa] [Homo sapiens]) and U18466 (ASU18466_8 pL270L [African swine fever virus]). Based upon sequence similarity, AM973_1 proteins and each similar protein or peptide may share at least some activity. The nucleotide sequence of AM973_1 indicates that it may contain an Alu repetitive element.

Clone "BK260 2"

A polynucleotide of the present invention has been identified as clone "BK260_2". BK260_2 was isolated from a human adult retina cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. BK260_2 is a full-length clone, including the entire coding sequence of a secreted protein (also referred to herein as "BK260_2 protein").

The nucleotide sequence of the 5' portion of BK260_2 as presently determined is reported in SEQ ID NO:3. What applicants presently believe is the proper reading frame for the coding region is indicated in SEQ ID NO:4. The predicted amino acid sequence of the BK260_2 protein corresponding to the foregoing nucleotide sequence is reported in SEQ ID NO:4. Additional nucleotide sequence from the 3' portion of BK260_2, including the poly A tail, is reported in SEQ ID NO:5.

The EcoRI/NotI restriction fragment obtainable from the deposit containing clone BK260_2 should be approximately 1900 bp.

The nucleotide sequence disclosed herein for BK260_2 was searched against the GenBank and GeneSeq nucleotide sequence databases using BLASTN/BLASTX and FASTA search protocols. BK260_2 demonstrated at least some similarity with sequences identified as N95713 (zb65b04.s1 Soares fetal lung NbHL19W Homo sapiens cDNA clone 308431 3') and T39242 (ya02f07.r2 Homo sapiens cDNA clone 60325 5'). Based upon sequence similarity, BK260_2 proteins and each similar protein or peptide may share at least some activity.

Clone "BR390 1"

A polynucleotide of the present invention has been identified as clone "BR390_1". BR390_1 was isolated from a human fetal kidney cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. BR390_1 is a full-length clone, including the entire coding sequence of a secreted protein (also referred to herein as "BR390_1 protein").

The nucleotide sequence of BR390_1 as presently determined is reported in SEQ ID NO:6. What applicants presently believe to be the proper reading frame and the predicted amino acid sequence of the BR390_1 protein corresponding to the foregoing nucleotide sequence is reported in SEQ ID NO:7. Amino acids 53 to 65 are a predicted leader/signal sequence, with the predicted mature amino acid sequence beginning at amino acid 66, or are a transmembrane domain.

The EcoRI/NotI restriction fragment obtainable from the deposit containing clone BR390_1 should be approximately 1100 bp.

The nucleotide sequence disclosed herein for BR390_1 was searched against the GenBank and GeneSeq nucleotide sequence databases using BLASTN/BLASTX and FASTA search protocols. BR390_1 demonstrated at least some similarity with sequences identified as AB007886 Homo sapiens KIAA0426 mRNA, complete cds), N53984 (yy99a08.r1 Homo sapiens cDNA clone 281654 5'), N66733 (yz33f03.s1 Homo sapiens cDNA clone 284861 3'), and R78314 (yi82c02.r1 Homo sapiens cDNA clone 145730 5'). Based upon sequence similarity, BR390_1 proteins and each similar protein or peptide may share at least some activity.

Clone "CJ539 3"

A polynucleotide of the present invention has been identified as clone "CJ539_3". CJ539_3 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CJ539_3 is a full-length clone, including the entire coding sequence of a secreted protein (also referred to herein as "CJ539_3 protein").

The nucleotide sequence of CJ539_3 as presently determined is reported in SEQ ID NO:8. What applicants presently believe to be the proper reading frame and the predicted amino acid sequence of the CJ539_3 protein corresponding to the foregoing nucleotide sequence is reported in SEQ ID NO:9. Amino acids 115 to 127 are a predicted leader/signal sequence, with the predicted mature amino acid sequence beginning at amino acid 128, or are a transmembrane domain.

The EcoRI/NotI restriction fragment obtainable from the deposit containing clone CJ539_3 should be approximately 3300 bp.

The nucleotide sequence disclosed herein for CJ539_3 was searched against the GenBank and GeneSeq nucleotide sequence databases using BLASTN/BLASTX and FASTA search protocols. CJ539_3 demonstrated at least some similarity with sequences identified as AA081798 (zn22g09.r1 Stratagene neuroepithelium NT2RAMI 937234 Homo sapiens cDNA clone 548224 5'), N56917 (yy82c03.s1 Homo sapiens cDNA clone 280036 3'), Q60395 (Human brain Expressed Sequence Tag EST02394), T06622 (EST04511 Homo sapiens cDNA clone HFBDW03), T74984 (yc85d06.r1 Homo sapiens cDNA clone 23018 5'), and W40170 (zc82h07.r1 Pancreatic Islet Homo sapiens cDNA clone 328861 5'). The predicted amino acid sequence disclosed herein for CJ539_3 was searched against the GenPept and GeneSeq amino acid sequence databases using the BLASTX search protocol. The predicted CJ539_3 protein demonstrated at least some similarity to sequences identified as L40587 (ubiquitin-like protein [Saccharomyces cerevisiae]), Z49704 (unknown [Saccharomyces cerevisiae]), Z71260 (F15C11.2 [Caenorhabditis elegans]), and Z98262 (F15C11.2 [Caenorhabditis elegans]). Based upon sequence similarity, CJ539_3 proteins and each similar protein or peptide may share at least some activity. The TopPredII computer program predicts two potential transmembrane domains within the CJ539_3 protein sequence, one centered around amino acid 120 and another around amino acid 460 of SEQ ID NO:9.

Clone "CN729 3"

A polynucleotide of the present invention has been identified as clone "CN729_3". CN729_3 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CN729_3 is a full-length clone, including the entire coding sequence of a secreted protein (also referred to herein as "CN729_3 protein").

The nucleotide sequence of CN729_3 as presently determined is reported in SEQ ID NO:10. What applicants presently believe to be the proper reading frame and the predicted amino acid sequence of the CN729_3 protein corresponding to the foregoing nucleotide sequence is reported in SEQ ID NO:11. Amino acids 31 to 43 are a predicted leader/signal sequence, with the predicted mature amino acid sequence beginning at amino acid 44, or are a transmembrane domain.

The EcoRI/NotI restriction fragment obtainable from the deposit containing clone CN729_3 should be approximately 3300 bp.

The nucleotide sequence disclosed herein for CN729_3 was searched against the GenBank and GeneSeq nucleotide sequence databases using BLASTN/BLASTX and FASTA search protocols. CN729_3 demonstrated at least some similarity with sequences identified as N30242 (yw64e08.s1 Homo sapiens cDNA clone 257030 3'), R35100 (yg59d11.r1 Homo sapiens cDNA clone 37156 5'), R96613 (yq54g11.r1 Homo sapiens cDNA clone 199652 5'), T77561 (yd73e09.r1 Homo sapiens cDNA clone 113896 5'), and U66088 (Human sodium iodide symporter mRNA, complete cds). The predicted amino acid sequence disclosed herein for CN729_3 was searched against the GenPept and GeneSeq amino acid sequence databases using the BLASTX search protocol. The predicted CN729_3 protein demonstrated at least some similarity to sequences identified as U60282 (Rattus norvegicus thyroid sodium/iodide symporter NIS mRNA, complete cds [Rattus norvegicus]) and U66088 (sodium iodide symporter [Homo sapiens]). Based upon sequence similarity, CN729_3 proteins and each similar protein or peptide may share at least some activity. The TopPredII computer program predicts at least twelve potential transmembrane domains within the CN729_3 protein sequence. The hydro-phobicity plots of CN729_3 and U66088 proteins are almost identical, further strengthening the idea that they have similar functions.

Clone "CO139 3"

A polynucleotide of the present invention has been identified as clone "CO139_3". CO139_3 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CO139_3 is a full-length clone, including the entire coding sequence of a secreted protein (also referred to herein as "CO139_3 protein").

The nucleotide sequence of CO139_3 as presently determined is reported in SEQ ID NO:12. What applicants presently believe to be the proper reading frame and the predicted amino acid sequence of the CO139_3 protein corresponding to the foregoing nucleotide sequence is reported in SEQ ID NO:13.

The EcoRI/NotI restriction fragment obtainable from the deposit containing clone CO139_3 should be approximately 3380 bp.

The nucleotide sequence disclosed herein for CO139_3 was searched against the GenBank and GeneSeq nucleotide sequence databases using BLASTN/BLASTX and FASTA search protocols. CO139_3 demonstrated at least some similarity with sequences identified as AA409680 (EST01443 Mouse 7.5 dpc embryo ectoplacental cone cDNA library Mus musculus cDNA clone C0009H07 5'), H17423 (ym40e10.r1 Homo sapiens cDNA clone 50502 5'), W40170 (zc82h07.r1 Pancreatic Islet Homo sapiens cDNA clone 328861 5'), and W45424 (zc82h07.s1 Pancreatic Islet Homo sapiens cDNA clone 328861 3'). Based upon sequence similarity, CO139_3 proteins and each similar protein or peptide may share at least some activity. The TopPredII computer program predicts a potential transmembrane domain within the CO139_3 protein sequence centered around amino acid 30 of SEQ ID NO:13.

Clone "CO1020 1"

A polynucleotide of the present invention has been identified as clone "CO1020_1". CO1020_1 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CO1020_1 is a full-length clone, including the entire coding sequence of a secreted protein (also referred to herein as "CO1020_1 protein").

The nucleotide sequence of CO1020_1 as presently determined is reported in SEQ ID NO:14. What applicants presently believe to be the proper reading frame and the predicted amino acid sequence of the CO1020_1 protein corresponding to the foregoing nucleotide sequence is reported in SEQ ID NO:15. Amino acids 257 to 269 of SEQ ID NO:15 are a predicted leader/signal sequence, with the predicted mature amino acid sequence beginning at amino acid 270, or are a transmembrane domain. Amino acids 57 to 69 of SEQ ID NO:15 are also a possible leader/signal sequence, with the predicted mature amino acid sequence beginning at amino acid 70. Another potential CO1020_1 reading frame and predicted amino acid sequence is encoded by basepairs 347 to 589 of SEQ ID NO:14 and is reported in SEQ ID NO:32.

The EcoRI/NotI restriction fragment obtainable from the deposit containing clone CO1020_1 should be approximately 2300 bp.

The nucleotide sequence disclosed herein for CO1020_1 was searched against the GenBank and GeneSeq nucleotide sequence databases using BLASTN/BLASTX and FASTA search protocols. CO1020_1 demonstrated at least some similarity with sequences identified as AA115333 (z109c09.r1 Soares pregnant uterus NbHPU Homo sapiens cDNA clone 501424 5'), AL009182 (Human DNA sequence * SEQUENCING IN PROGRESS * from clone 782G3; HTGS phase 1), R54280 (yg78d01.r1 Homo sapiens cDNA clone 39678 5'), and R54285 (yg78e01.r1 Homo sapiens cDNA clone 39372 5'). Based upon sequence similarity, CO1020_1 proteins and each similar protein or peptide may share at least some activity.

Clone "CS752 3"

A polynucleotide of the present invention has been identified as clone "CS752_3". CS752_3 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino add sequence of the encoded protein. CS752_3 is a full-length clone, including the entire coding sequence of a secreted protein (also referred to herein as "CS752_3 protein").

The nucleotide sequence of CS752_3 as presently determined is reported in SEQ ID NO:16. What applicants presently believe to be the proper reading frame and the predicted amino acid sequence of the CS752_3 protein corresponding to the foregoing nucleotide sequence is reported in SEQ ID NO:17. Amino acids 63 to 75 are a predicted leader/signal sequence, with the predicted mature amino acid sequence beginning at amino acid 76, or are a transmembrane domain.

The EcoRI/NotI restriction fragment obtainable from the deposit containing clone CS752_3 should be approximately 1700 bp.

The nucleotide sequence disclosed herein for CS752_3 was searched against the GenBank and GeneSeq nucleotide sequence databases using BLASTN/BLASTX and FASTA search protocols. CS752_3 demonstrated at least some similarity with sequences identified as AA614644 (np54d05.s1 NCI_CGAP_Br1.1 Homo sapiens cDNA clone IMAGE:1130121), L44447 (Homo sapiens thymus MRNA (randomly primed, normalized), single-pass sequence), R27192 (yh52b11.r1 Homo sapiens cDNA clone 133341 5'), and W69395 (zd46b12.s1 Soares fetal heart NbHH19W Homo sapiens cDNA clone 343679 3'). The predicted amino acid sequence disclosed herein for CS752_3 was searched against the GenPept and GeneSeq amino acid sequence databases using the BLASTX search protocol. The predicted CS752_3 protein demonstrated at least some similarity to sequences identified as Z80215 (C36B1.12 [Caenorhabditis elegans]). Based upon sequence similarity, CS752_3 proteins and each similar protein or peptide may share at least some activity. The TopPredII computer program predicts four potential transmembrane domains within the CS752_3 protein sequence centered one around amino acids 75, 125, 180, and 230 of SEQ ID NO:17, respectively.

Clone "DM340 1"

A polynucleotide of the present invention has been identified as clone "DM340_1". DM340_1 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. DM340_1 is a full-length clone, including the entire coding sequence of a secreted protein (also referred to herein as "DM340_1 protein").

The nucleotide sequence of DM340_1 as presently determined is reported in SEQ ID NO:18. What applicants presently believe to be the proper reading frame and the predicted amino acid sequence of the DM340_1 protein corresponding to the foregoing nucleotide sequence is reported in SEQ ID NO:19. Amino acids 10 to 22 are a predicted leader/signal sequence, with the predicted mature amino acid sequence beginning at amino acid 23, or are a transmembrane domain.

The EcoRI/NotI restriction fragment obtainable from the deposit containing clone DM340_1 should be approximately 1800 bp.

The nucleotide sequence disclosed herein for DM340_1 was searched against the GenBank and GeneSeq nucleotide sequence databases using BLASTN/BLASTX and FASTA search protocols. DM340_1 demonstrated at least some similarity with sequences identified as AA049712 (mj13a01.r1 Soares mouse embryo NbME13.5 14.5 Mus musculus cDNA clone 475944 5' similar to SW PC1_HUMAN P22413 PLASMA-CELL MEMBRANE GLYCOPROTEIN PC-1). The predicted amino acid sequence disclosed herein for DM340_1 was searched against the GenPept and GeneSeq amino acid sequence databases using the BLASTX search protocol. The predicted DM340_1 protein demonstrated at least some similarity to sequences identified as D30649 (phosphodiesterase I [Rattus rattus]), R79148 (Human insulin receptor tyrosine kinase inhibitor PC-1), U78787 (alkaline phosphodiesterase [Rattus norvegicus]), and Z47987 (RB13-6 antigen [Rattus norvegicus]). Based upon sequence similarity, DM340_1 proteins and each similar protein or peptide may share at least some activity.

Clone "DW902 1"

A polynucleotide of the present invention has been identified as clone "DW902_1". DW902_1 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. DW902_1 is a full-length clone, including the entire coding sequence of a secreted protein (also referred to herein as "DW902_1 protein").

The nucleotide sequence of DW902_1 as presently determined is reported in SEQ ID NO:20. What applicants presently believe to be the proper reading frame and the predicted amino acid sequence of the DW902_1 protein corresponding to the foregoing nucleotide sequence is reported in SEQ ID NO:21.

The EcoRI/NotI restriction fragment obtainable from the deposit containing clone DW902_1 should be approximately 3650 bp.

The nucleotide sequence disclosed herein for DW902_1 was searched against the GenBank and GeneSeq nucleotide sequence databases using BLASTN/BLASTX and FASTA search protocols. DW902_1 demonstrated at least some similarity with sequences identified as AA651956 (ns39h09.s1 NCI_CGAP_GCB1 Homo sapiens cDNA clone IMAGE:1186049), N50020 (yz10a03.s1 Homo sapiens cDNA clone 282604 3'), R62449 (yg53b10.s1 Homo sapiens cDNA clone 36462 3'), and W59499 (ma36a07.r1 Life Tech mouse brain Mus musculus cDNA clone 312756 5'). Based upon sequence similarity, DW902_1 proteins and each similar protein or peptide may share at least some activity.

Deposit of Clones

Clones AM973_1, BK260_2, BR390_1, CJ539_3, CN729_3, CO139_3, CO1020_1, CS752_3, DM340_1, and DW902_1 were deposited on Jan. 30, 1997 with the American Type Culture Collection (10801 University Boulevard, Manassas, Va. 20110-2209 USA) as an original deposit under the Budapest Treaty and were given the accession number ATCC 98311, from which each clone comprising a particular polynucleotide is obtainable. All restrictions on the availability to the public of the deposited material will be irrevocably removed upon the granting of the patent, except for the requirements specified in 37 C.F.R. § 1.808(b).

Figure 1B:
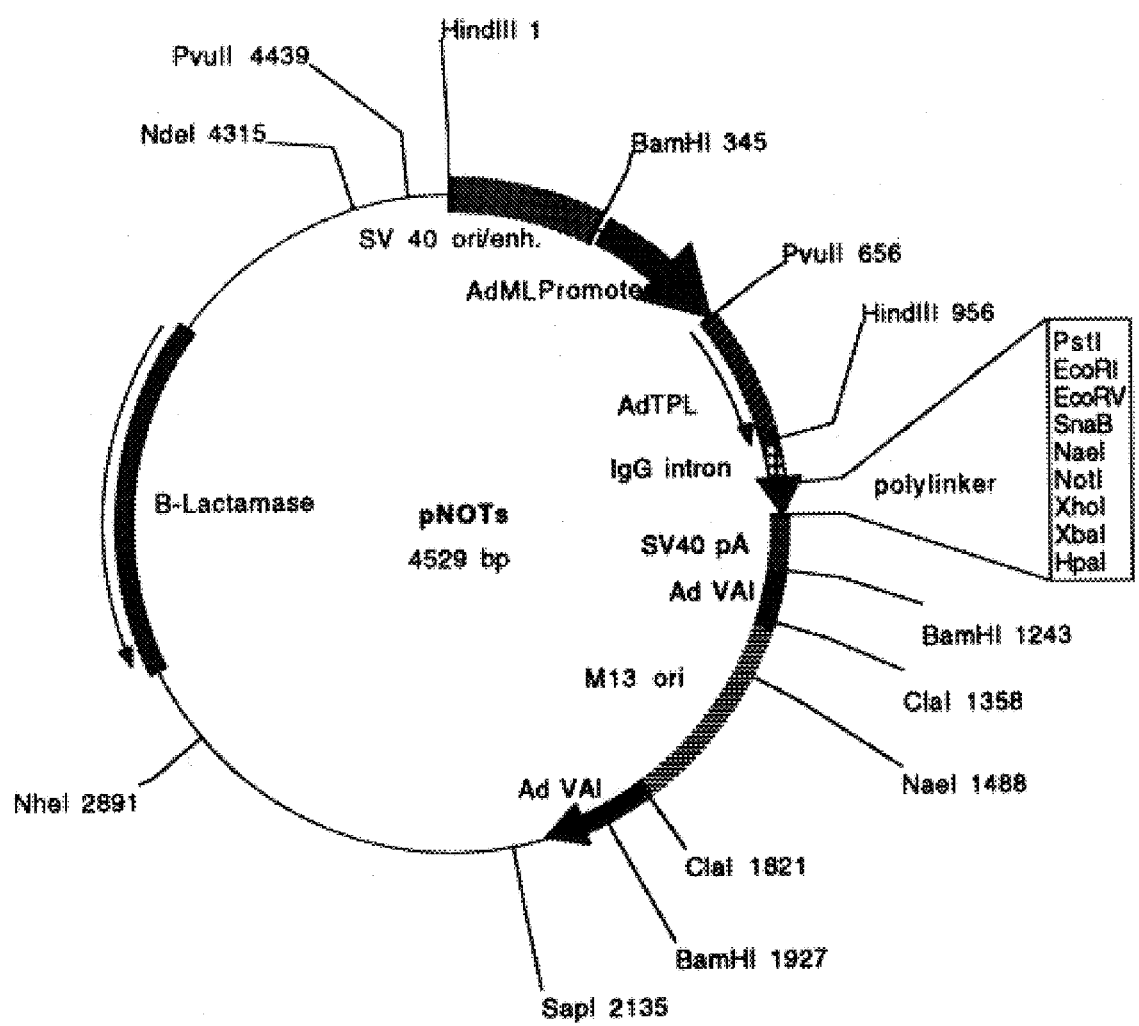

Each clone has been transfected into separate bacterial cells (E. coli) in this composite deposit. Each clone can be removed from the vector in which it was deposited by performing an EcoRI/NotI digestion (5' site, EcoRI; 3' site, NotI) to produce the appropriate fragment for such clone. Each clone was deposited in either the pED6 or pNOTs vector depicted in FIG. 1. The pED6dpc2 vector ("pED6") was derived from pED6dpc1 by insertion of a new polylinker to facilitate cDNA cloning (Kaufman et al., 1991, *Nucleic Acids Res.* 19: 4485–4490); the pNOTs vector was derived from pMT2 (Kaufman et al., 1989, *Mol. Cell. Biol.* 9: 946–958) by deletion of the DHPR sequences, insertion of a new polylinker, and insertion of the M13 origin of replication in the ClaI site. In some instances, the deposited clone can become "flipped" (i.e., in the reverse orientation) in the deposited isolate. In such instances, the cDNA insert can still be isolated by digestion with EcoRI and NotI. However, NotI will then produce the 5' site and EcoRI will produce the 3' site for placement of the cDNA in proper orientation for expression in a suitable vector. The cDNA may also be expressed from the vectors in which they were deposited.

Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The sequence of the oligonucleotide probe that was used to isolate each full-length clone is identified below, and should be most reliable in isolating the clone of interest.

| Clone | Probe Sequence |
|---|---|
| AM973_1 | SEQ ID NO:22 |
| BK260_2 | SEQ ID NO:23 |
| BR390_1 | SEQ ID NO:24 |
| CJ539_3 | SEQ ID NO:25 |
| CN729_3 | SEQ ID NO:26 |
| CO139_3 | SEQ ID NO:27 |
| CO1020_1 | SEQ ID NO:28 |
| CS752_3 | SEQ ID NO:29 |
| DM340_1 | SEQ ID NO:30 |
| DW902_1 | SEQ ID NO:31 |

In the sequences listed above which include an N at position 2, that position is occupied in preferred probes/primers by a biotinylated phosphoaramidite residue rather than a nucleotide (such as , for example, that produced by use of biotin phosphoramidite (1-dimethoxytrityloxy-2-(N-biotinyl-4-aminobutyl)-propyl-3-0-(2-cyanoethyl)–(N,N-diisopropyl)-phosphoramadite) (Glen Research, cat. no. 10-1953)).

The design of the oligonucleotide probe should preferably follow these parameters:

(a) It should be designed to an area of the sequence which has the fewest ambiguous bases ("N's"), if any;

(b) It should be designed to have a $T_m$ of approx. 80° C. (assuming 2° for each A or T and 4 degrees for each G or C).

The oligonucleotide should preferably be labeled with g-$^{32}$P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/pmole.

The bacterial culture containing the pool of full-length clones should preferably be thawed and 100 μl of the stock used to inoculate a sterile culture flask containing 25 ml of sterile L-broth containing ampicillin at 100 μg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 μg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6X SSC (20X stock is 175.3 g NaCl/liter, 88.2 g Na citrate/liter, adjusted to pH 7.0 with NaOH) containing 0.5% SDS, 100 μg/ml of yeast RNA, and 10 mM EDTA (approximately 10 mL per 150 mm filter). Preferably, the probe is then added to the hybridization mix at a concentration greater than or equal to 1e+6 dpm/mL. The filter is then preferably incubated at 65° C. with gentle agitation overnight. The filter is then preferably washed in 500 mL of 2X SSC/0.5% SDS at room temperature without agitation, preferably followed by 500 mL of 2X SSC/0.1% SDS at room temperature with gentle shaking for 15 minutes. A third wash with 0.1X SSC/0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form of such protein may be obtained by expression of the disclosed full-length polynucleotide (preferably those deposited with ATCC) in a suitable mammalian cell or other host cell. The sequence of the mature form of the protein may also be determinable from the amino acid sequence of the full-length form.

The present invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

Organisms that have enhanced, reduced, or modified expression of the gene(s) corresponding to the polynucleotide sequences disclosed herein are provided. The desired change in gene expression can be achieved through the use of antisense polynucleotides or ribozymes that bind and/or cleave the MRNA transcribed from the gene (Albert and Morris, 1994, *Trends Pharmacol. Sci.* 15(7):250–254; Lavarosky et al., 1997, *Biochem. Mol. Med.* 62(1):11–22; and Hampel, 1998, *Prog. Nucleic Acid Res. Mol. Biol.* 58: 1–39; all of which are incorporated by reference herein). Transgenic animals that have multiple copies of the gene(s) corresponding to the polynucleotide sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, *Bioessays* 14(9) :629–633; Zwaal et al., 1993, *Proc. Natl. Acad. Sci. USA* 90(16):7431–7435; Clark et al., 1994, *Proc. Natl. Acad. Sci. USA* 91(2):719–722; all of which are incorporated by reference herein), or through homologous recombination, preferably detected by positive/negative genetic selection strategies (Mansour et al., 1988, *Nature* 336: 348–352; U.S. Pat. Nos. 5,464,764; 5,487,992; 5,627,059; 5,631,153; 5,614, 396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the protein product(s) of the corresponding gene(s).

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

Species homologs of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide, as determined by those of skill in the art. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous, or related to that encoded by the polynucleotides.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | ≥50 | 67° C.; 1xSSC -or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | ≥50 | 70° C.; 1xSSC -or- 50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | ≥50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≥50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≥50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≥50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≥50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≥50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.

*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$ (° C.) = 2 (# of A + T bases) + 4 (# of G + C bases). For hybrids between 18 and 49 base pairs in length, $T_m$ (° C.) = 81.5 + 16.6 ($\log_{10}$ [$Na^+$]) + 0.41 (% G + C). − (600/N), where N is the number of bases in the hybrid, and [$Na^+$] is the concentration of sodium ions in the hybridization buffer ([$Na^+$] for 1xSSC = 0.165M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3–6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces strains, Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, erg., Invitrogen, San Diego, Calif., U.S.A. (the MaxBac® kit), and such methods are well known in the art, as described in Summers and Smith, *Texas Agricultural Experiment Station Bulletin No. 1555* (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

USES AND BIOLOGICAL ACTIVITY

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit formnat for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Intersdence (Chapter 3, In Vitro assays for Mouse Lymphocyte Function 3.1–3.19; Chapter 7, Immunologic studies in Humans); Takai et al., J. Immunol. 137:3494–3500, 1986; Bertagnolr et al., J. Immunol. 145:1706–1712, 1990; Bertagnolr et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human Interferon γ, Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lip sky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6 - Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11 - Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9 - Ciarletta, A., Giannotti, J., Clark, S. C. and Turner, K. J. In Current Protocols in Immunology. J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or energy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnori et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In *Current Protocols in Immunology*. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell cominntment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation- hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In *Culture of Hematopoietic Cells.* R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In *Culture of Hematopoietic Cells.* R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells.* R. I. Freshney, et al. eds. Vol pp. 1–21, Wiley-Liss, Inc.., New York, N.Y. 1994; Long term bone marrow cultures in the presence of stromal cells, Spooncer, E., Dexter, M. and Allen, T. In *Culture of Hematopoietic Cells.* R. I. Freshney, et al. eds. Vol pp. 163–179, Wiley-Liss, Inc., New York, N.Y. 1994; Long term culture initiating cell assay, Sutherland, H. J. In *Culture of Hematopoietic Cells.* R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing* pps. 71–112 (Maibach, H I and Rovee, D T, eds.), Year Book Medical Publishers, Inc., Chicago, as modified by Eaglstein and Mertz, J. Invest. Dermatol 71:382–84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating PSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744–1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419,1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selecting, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in:Current Protocols in Immunology, Ed by J. E. Coligan, A. M. Kruisbeek, D. H. Margulies, E. M. Shevach, W. Strober, Pub. Greene Publishing Associates and Wiley-lnterscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Cadherin/Tumor Invasion Suppressor Activity

Cadherins are calcium-dependent adhesion molecules that appear to play major roles during development, particularly in defining specific cell types. Loss or alteration of normal cadherin expression can lead to changes in cell adhesion properties linked to tumor growth and metastasis. Cadherin malfunction is also implicated in other human diseases, such as pemphigus vulgaris and pemphigus foliaceus (autoimmune blistering skin diseases), Crohn's disease, and some developmental abnormalities.

The cadherin superfamily includes well over forty members, each with a distinct pattern of expression. All members of the superfamily have in common conserved extracellular repeats (cadherin domains), but structural differences are found in other parts of the molecule. The cadherin domains bind calcium to form their tertiary structure and thus calcium is required to mediate their adhesion. Only a few amino acids in the first cadherin domain provide the basis for homophilic adhesion; modification of this recognition site can change the specificity of a cadherin so that instead of recognizing only itself, the mutant molecule can now also bind to a different cadherin. In addition, some cadherins engage in heterophilic adhesion with other cadherins.

E-cadherin, one member of the cadherin superfamily, is expressed in epithelial cell types. Pathologically, if E-cadherin expression is lost in a tumor, the malignant cells become invasive and the cancer metastasizes. Transfection of cancer cell lines with polynucleotides expressing E-cadherin has reversed cancer-associated changes by returning altered cell shapes to normal, restoring cells' adhesiveness to each other and to their substrate, decreasing the cell growth rate, and drastically reducing anchorage-independent cell growth. Thus, reintroducing E-cadherin expression reverts carcinomas to a less advanced stage. It is likely that other cadherins have the same invasion suppressor role in carcinomas derived from other tissue types. Therefore, proteins of the present invention with cadherin activity, and polynucleotides of the present invention encoding such proteins, can be used to treat cancer. Introducing such proteins or polynucleotides into cancer cells can reduce or eliminate the cancerous changes observed in these cells by providing normal cadherin expression.

Cancer cells have also been shown to express cadherins of a different tissue type than their origin, thus allowing these cells to invade and metastasize in a different tissue in the body. Proteins of the present invention with cadherin activity, and polynucleotides of the present invention encoding such proteins, can be substituted in these cells for the inappropriately expressed cadherins, restoring normal cell adhesive properties and reducing or eliminating the tendency of the cells to metastasize.

Additionally, proteins of the present invention with cadherin activity, and polynucleotides of the present invention encoding such proteins, can used to generate antibodies recognizing and binding to cadherins. Such antibodies can be used to block the adhesion of inappropriately expressed tumor-cell cadherins, preventing the cells from forming a tumor elsewhere. Such an anti-cadherin antibody can also be used as a marker for the grade, pathological type, and prognosis of a cancer, i.e. the more progressed the cancer, the less cadherin expression there will be, and this decrease in cadherin expression can be detected by the use of a cadherin-binding antibody.

Fragments of proteins of the present invention with cadherin activity, preferably a polypeptide comprising a decapeptide of the cadherin recognition site, and polynucleotides of the present invention encoding such protein fragments, can also be used to block cadherin function by binding to cadherins and preventing them from binding in ways that produce undesirable effects. Additionally, fragments of proteins of the present invention with cadherin activity, preferably truncated soluble cadherin fragments which have been found to be stable in the circulation of cancer patients, and polynucleotides encoding such protein fragments, can be used to disturb proper cell-cell adhesion.

Assays for cadherin adhesive and invasive suppressor activity include, without limitation, those described in: Hortsch et al. J Biol Chem 270 (32): 18809–18817, 1995; Miyaki et al. Oncogene 11: 2547–2552, 1995; Ozawa et al. Cell 63: 1033–1038, 1990.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

ADMINISTRATION AND DOSING

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL4, IL-5, IL-6, IL-7, IL-8, IL-9, IL-10, IL-11, IL-12, IL-13, IL-14, IL-15, EFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 ng to about 10 mg, more preferably about 0.1 $\mu$g to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-A and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

Patent and literature references cited herein are incorporated by reference as if fully set forth.

What is claimed is:

1. An isolated polynucleotide selected from the group consisting of:
   (a) a polynucleotide comprising the nucleotide sequence of SEQ ID NO: 1;
   (b) a polynucleotide comprising the nucleotide sequence of SEQ ID NO: 1 from nucleotide 374 to nucleotide 505;
   (c) a polynucleotide comprising the nucleotide sequence of SEQ ID NO: 1 from nucleotide 374 to nucleotide 518;
   (d) a polynucleotide comprising the nucleotide sequence of the full-length protein coding sequence of clone AM973_1 deposited under accession number ATCC 98311;
   (e) a polynucleotide encoding the full-length protein encoded by the cDNA insert of clone AM973_1 deposited under accession number ATCC 98311;
   (f) a polynucleotide encoding a protein comprising the amino acid sequence of SEQ ID NO:2;
   (g) a polynucleotide encoding a protein comprising a fragment of the amino acid sequence of SEQ ID NO:2, the fragment comprising eight consecutive amino add of SEQ ID NO:2; and
   (h) a polynucleotide that hybridizes in 6X SSC at 65 degrees C. to any one of the polynucleotides specified in (b)–(g).

2. The polynucleotide of claim 1 wherein said polynucleotide is operably linked to at least one expression control sequence.

3. A host cell transformed with the polynucleotide of claim 2.

4. The host cell of claim 3, wherein said cell is a mammalian cell.

5. A process for producing a protein encoded by the polynucleotide of claim 2, which process comprises:
   (a) growing a culture of the host cell of claim 3 in a suitable culture medium; and
   (b) purifying said protein from the culture.

6. An isolated polynucleotide encoding a protein, wherein the protein is produced according to the process of claim 5.

7. The polynucleotide of claim 6, wherein the polynucleotide comprises the cDNA insert of clone AM973_1 deposited under accession number ATCC 98311.

8. The polynucleotide of claim 1, wherein the polynucleotide comprises the nucleotide sequence of SEQ ID NO: 1.

9. The polynucleotide of claim 1, wherein the polynucleotide comprises the nucleotide sequence of SEQ ID NO:1 from nucleotide 374 to nucleotide 505.

10. The polynucleotide of claim 1, wherein the polynucleotide comprises the nucleotide sequence of SEQ ID NO: 1 from nucleotide 374 to nucleotide 518.

11. The polynucleotide of claim 1, wherein the polynucleotide comprises the nucleotide sequence of the full-length protein coding sequence of clone AM973_1 deposited under accession number ATCC 98311.

12. The polynucleotide of claim 1, wherein the polynucleotide encodes the full-length protein encoded by the cDNA insert of clone AM973_1 deposited under accession number ATCC 98311.

13. The polynucleotide of claim 1, wherein the polynucleotide encodes a protein comprising the amino acid sequence of SEQ ID NO:2.

14. The polynucleotide of claim 1, wherein the polynucleotide encodes a protein comprising a fragment of the amino acid sequence of SEQ ID NO:2, the fragment comprising eight contiguous amino acids of SEQ ID NO:2.

* * * * *